US011521746B1

(12) United States Patent
Weintraub

(10) Patent No.: US 11,521,746 B1
(45) Date of Patent: Dec. 6, 2022

(54) APPARATUS AND METHODS FOR CAUSING PRIVACY-SENSITIVE DIRECTION OF ADVERTISING MESSAGES BASED ON PREVALENCE OF A HEALTHCARE CONDITION IN A PLURALITY OF GEOGRAPHIC AREAS

(71) Applicant: Michael D Weintraub, Scottsdale, AZ (US)

(72) Inventor: Michael D Weintraub, Scottsdale, AZ (US)

(*) Notice: Subject to any disclaimer, the term of this patent is extended or adjusted under 35 U.S.C. 154(b) by 876 days.

(21) Appl. No.: 16/382,989

(22) Filed: Apr. 12, 2019

Related U.S. Application Data

(63) Continuation of application No. 14/496,467, filed on Sep. 25, 2014, now Pat. No. 10,262,761, which is a continuation of application No. 12/651,416, filed on Dec. 31, 2009, now abandoned.

(60) Provisional application No. 61/244,565, filed on Sep. 22, 2009, provisional application No. 61/142,315, filed on Jan. 2, 2009, provisional application No. 61/142,217, filed on Jan. 1, 2009.

(51) Int. Cl.
*G06Q 30/00* (2012.01)
*G16H 50/30* (2018.01)
*G06Q 30/02* (2012.01)

(52) U.S. Cl.
CPC ......... *G16H 50/30* (2018.01); *G06Q 30/0242* (2013.01); *G06Q 30/0269* (2013.01)

(58) Field of Classification Search
None
See application file for complete search history.

(56) References Cited

U.S. PATENT DOCUMENTS 8,131,585 B2 * 3/2012 Nicholas ............ G06Q 30/0261
705/14.58

OTHER PUBLICATIONS

Martin; The Role of Law in Control of Obesity; New Zealand Health Policy; 12 pages; Oct. 14, 2008.*
Wen; The_evolving_face_of_telemedicine_amp_e-health; IEEE HICCSS'03; 12 pages; Mar. 2003.*

* cited by examiner

*Primary Examiner* — Radu Andrei
(74) *Attorney, Agent, or Firm* — Louis J. Hoffman

(57) ABSTRACT

A computer system and method causes selection of an advertisement based on the prevalence of a healthcare condition in each of a plurality of geographic areas. The prevalence is calculated by an entity that matches healthcare data with consumer data to determine, in each of the geographic areas, how many individuals have an unidentified healthcare condition. The entity removes information pertaining to specific geographic areas and healthcare condition codes that would permit re-identification of persons coded with those specific codes, so that the privacy of the personal healthcare information is maintained.

16 Claims, 20 Drawing Sheets

| Key   | Name         | Address                             | Phone          | SSN         |
|-------|--------------|-------------------------------------|----------------|-------------|
| L3w93 | John Jones   | 123 Main St., Phoenix, AZ 85250     | (480)555-1212  | 999-33-9999 |
| EYB6s | Bob Smith    | 456 Anystreet, Los Angeles, CA 03833 | (302)777-9876  | 999-44-7773 |
| Nr4BP | Grant Barker | 2029 Country Ln, Anytown, MD 97837  | (402)614-3423  | 333-66-6654 |
| ...   | ...          | ...                                 | ...            | ...         |
| $n$   | $n$          | $n$                                 | $n$            | $n$         |

FIG 5A

| Key   | Expression |
|-------|------------|
| L3w93 | 1          |
| EYB6s | 0          |
| Nr4BP | 0          |
| ...   | ...        |
| $n$   | (0,1)      |

FIG 5B

| Condition                                  | Expression |
|--------------------------------------------|------------|
| Positive for Arthritis and NSAID treatment | 0          |
| Negative for Arthritis and NSAID treatment | 1          |

FIG 5C

| Name | Address | Phone | ZIP+4 | email |
|---|---|---|---|---|
| John Jones | 123 Main St., Phoenix, AZ 85250 | (480)555-1212 | 822501245 | jjones@cox.net |
| Bob Smith | 456 Anystreet, Los Angeles, CA 03833 | (302)777-9876 | 038334534 | bob@smith.com |
| Grant Barker | 2029 Country Ln, Anytown, MD 97837 | (402)614-3423 | 978373321 | gb@ibm.com |
| ... | ... | ... | | ... |
| n | n | n | | n |

FIG 7A

| Zip+4 | IP Ranges | Lat and Long | Percentage |
|---|---|---|---|
| 822501245 | 192.168.7.0/24 | 33.5988 111.7413 | 50 |
| 038334534 | 127.127.0.0/16 | 42.9832 70.9915 | 2 |
| 978373321 | 172.16.12.0/24, 127.16.13.0/24 | 44.6096 118.0303 | 60 |
| ... | | | ... |
| n | | | n |

FIG 7B

| Period | IP | Ad | Test or Control | New Patients | RXs | AWP |
|---|---|---|---|---|---|---|
| 1 | 10.1.1.5 | n/a | Test | 1 | 12 | 60 |
| 1 | #1 | n/a | Control | 0 | 0 | 0 |
| 1 | 10.1.68.99 | n/a | Test | 2 | 24 | 120 |
| 1 | #2 | n/a | Control | 1 | 12 | 60 |
| 1 | 192.168.14.2 | n/a | Test | 1 | 24 | 120 |
| 1 | #3 | n/a | Control | 0 | 12a | 60 |
| 2 | 10.1.1.5 | 1 | Test | 2 | 18 | 90 |
| 2 | #1 | n/a | Control | 1 | 6 | 30 |
| 2 | 10.1.68.99 | 1 | Test | 2 | 24 | 120 |
| 2 | #2 | n/a | Control | 1 | 12 | 60 |
| 2 | 192.168.14.2 | 2 | Test | 2 | 36 | 180 |
| 2 | #3 | n/a | Control | 0 | 12 | 60 |
| ... | ... | ... | ... | ... | ... | ... |
| n | n | n | n | n | n | n |

FIG 11A

| Period | Test/Control | Impressions | Cost/Impression | AWP | Test/Control Difference | ROI |
|---|---|---|---|---|---|---|
| 1 | Test | n/a | n/a | $300 | ($300-$120) = $180 | |
| 1 | Control | n/a | n/a | $120 | n/a | |
| 2 | Test | 3 | $2 | $390 | ($390-$150) = $240 | ($240-$180)/$6=1000% |
| 2 | Control | n/a | n/a | $150 | n/a | |

FIG 11B

| Ad | Impressions | RXs | RXs/Impression |
|---|---|---|---|
| 1 | 2 | 42 | 42/2=21 |
| 2 | 1 | 36 | 26/1=36 |

FIG 11C

APPARATUS AND METHODS FOR CAUSING PRIVACY-SENSITIVE DIRECTION OF ADVERTISING MESSAGES BASED ON PREVALENCE OF A HEALTHCARE CONDITION IN A PLURALITY OF GEOGRAPHIC AREAS

CROSS REFERENCE TO RELATED APPLICATIONS

This application is a continuation of application Ser. No. 14/496,467, filed Sep. 25, 2014, now U.S. Pat. No. 10,262,761, which is a continuation of application Ser. No. 12/651,416, filed Dec. 31, 2009, now abandoned, which claims benefit of provisional application Ser. No. 61/142,217, filed Jan. 1, 2009, provisional application Ser. No. 61/142,315, filed Jan. 2, 2009, and provisional application Ser. No. 61/244,565, filed Sep. 22, 2009, which provisional applications are hereby incorporated by reference as if fully set forth herein.

BRIEF DESCRIPTION OF THE DRAWINGS

FIGS. 5A-5C show data structure layouts illustrating example values of data transmitted between the consumer household database and the healthcare database, according to an embodiment.

FIGS. 7A and 7B show data structure layouts illustrating example values of electronic lists for automatically transmitting messages to geographical areas corresponding to selected health conditions and demographic conditions, according to an embodiment.

FIGS. 11A-11C show data structure layout diagrams illustrating example values of electronic lists for tracking information helpful in determining an outcome of a healthcare advertisement, according to an embodiment.

DETAILED DESCRIPTION

In the following description, numerous specific details are set forth illustrating the inventor's best mode for practicing the disclosed systems and enabling one of ordinary skill in the art to make and use them. It will be obvious, however, to one skilled in the art that the disclosed systems may be practiced without many of these specific details. In other instances, well-known software systems, software methods, business methods, statistical methods, and other method steps have not been described in particular detail in order to avoid unnecessarily obscuring this disclosure.

Figure 1:
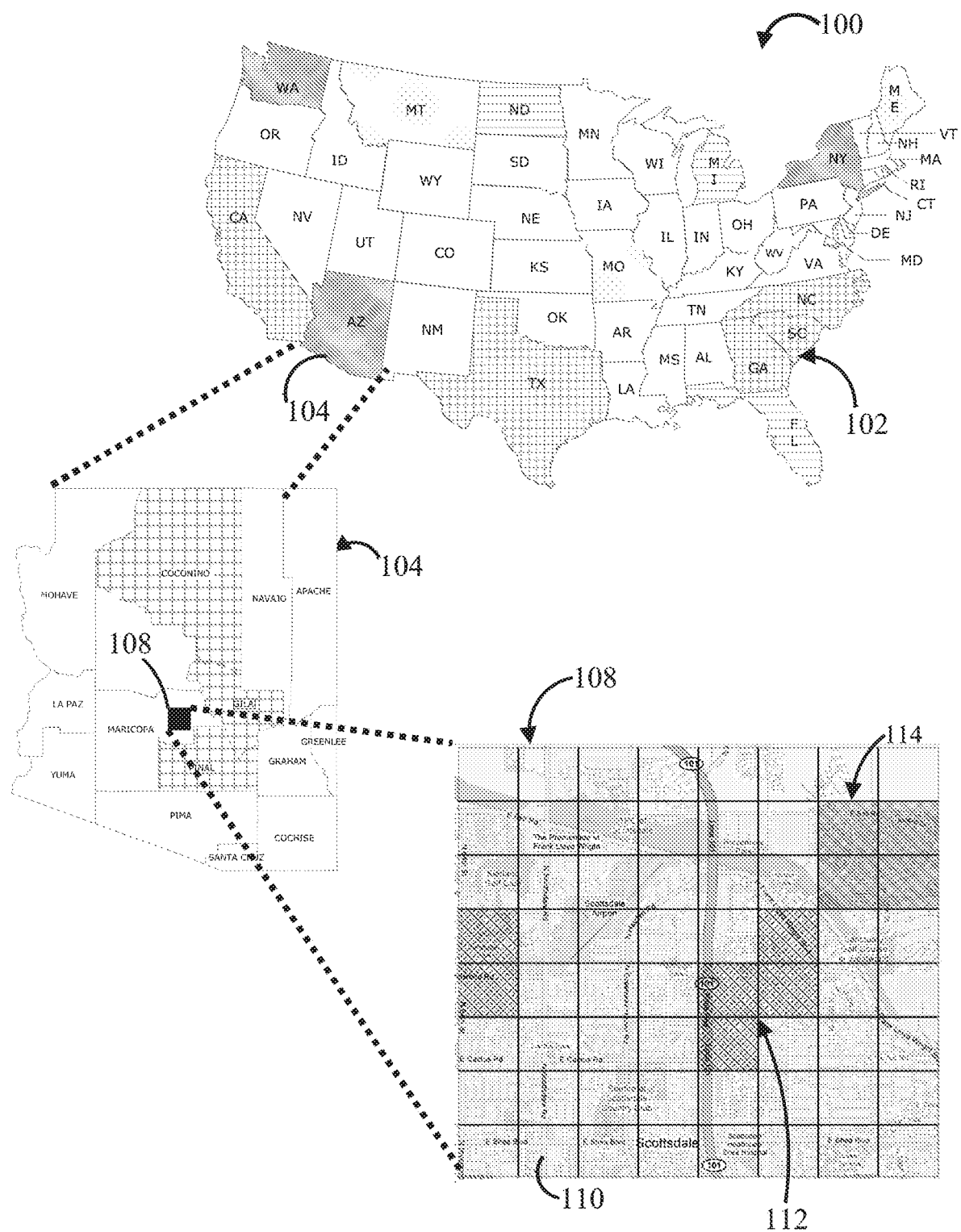
FIG. 1 shows a diagrammatic view illustrating a geographical map showing probability of a specified health condition across geographical locations and associated demographic information, according to an embodiment.

FIG. 1 shows a diagrammatic view illustrating geographical map 100 showing probability of a specified health condition across geographical locations and associated demographic information, according to an embodiment. Geographical map 100 shows the relationship between a health condition, consumer demographic data, and geographical location. Geographical map 100 contains stippling patterns to indicate that certain geographical regions are statistically likely to have a specified concentration of people who experience a specified health condition and have a specified demographic profile. For example, a query could be formed to determine geographical areas in which a minimum of 20% of the individuals or households have received a diagnosis of arthritis, have been prescribed non-steroidal anti-inflammatory drugs, and regularly clip coupons.

By way of example, the map has been shaded to show geographical areas where those conditions have been met. Top-level map 102 may show broad geographic areas that meet those conditions. Sub-region map 104 may show counties, cities, or other relatively large geographical subdivisions that meet those conditions. Street-level map 108 may show city blocks, Zip+4 areas, or even specific buildings (that have sufficiently large numbers of individuals or households) where those conditions have been met. An embodiment may determine whether those conditions have been met by compiling health condition and demographic data in such a way that the data may not be later used to determine that a specific individual has the health condition, thereby preserving the confidentiality of the healthcare data and the privacy of the individuals who live in the geographic area. For example, area 110 (which may correspond to a Zip+4 area, proper name of a geographical subdivision, area defined by latitude and longitude boundaries, etc.) shows no likelihood of the condition in this area, hence it is not stippled. For example, area 112 shows a higher probability of the condition, as seen by the light stippling pattern. For example, area 114 of street-level map 108 shows the highest probability of the condition, as seen by the dark stippling pattern. FIG. 1 displays the information graphically, but the information may be used electronically by embodiments to automatically or manually send messages to the residents of the geographic area. This information may also be used for research purposes.

Figure 2:
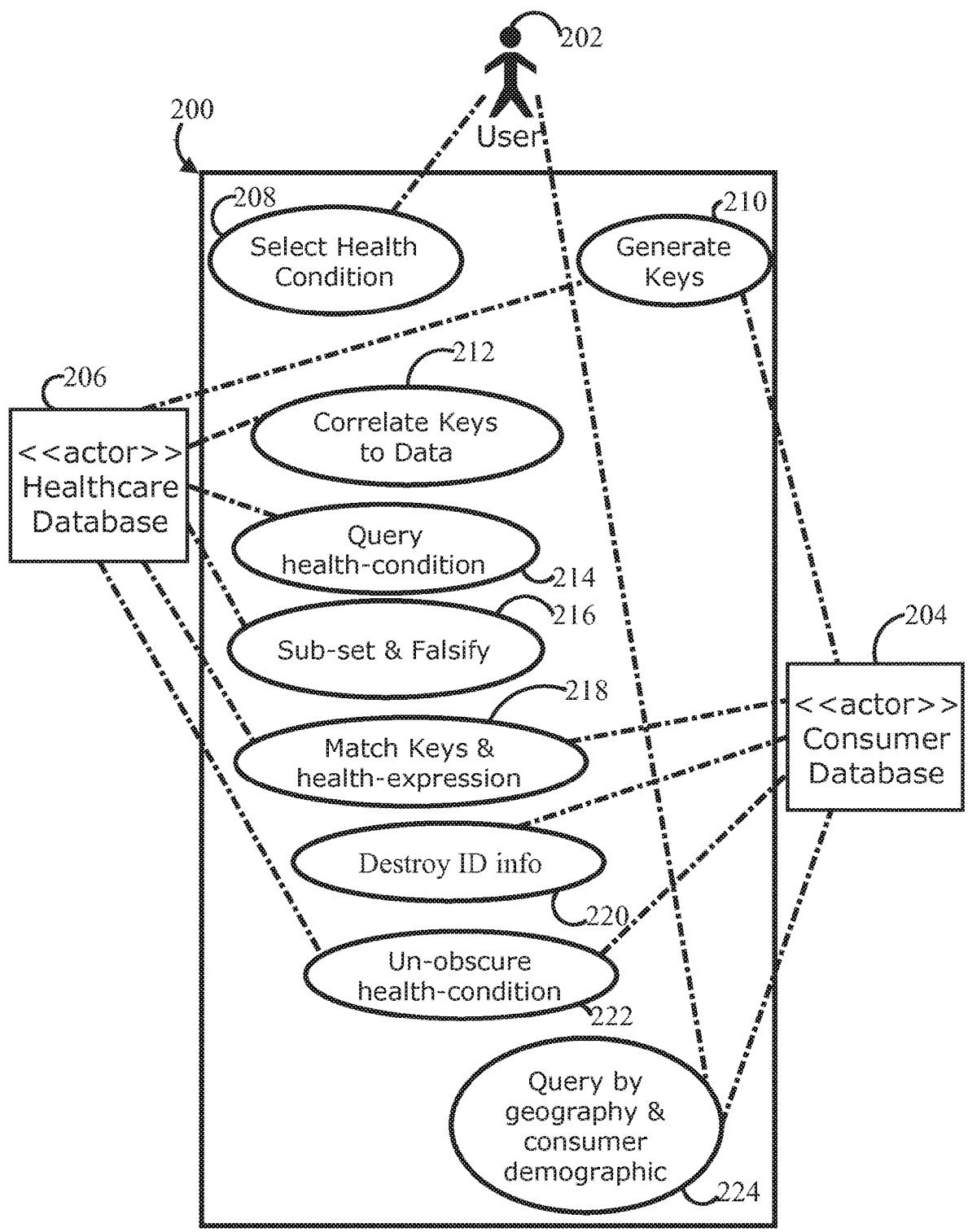
FIG. 2 shows a use case diagram illustrating functions of an embodiment that combines health condition information with consumer demographic information while statistically insuring that the identity of individuals cannot be known.

FIG. 2 shows a use case diagram illustrating functions of an embodiment (system 200) that combines health condition information with consumer demographic information while statistically ensuring that the identity of individuals cannot be known. System 200 may be acted on by user 202, consumer-database 204, and healthcare-database 206. User 202 may invoke function select-health-condition 208 to indicate to system 200 that user 202 would like a list of geographical areas with a specified concentration of the health condition. The health condition may be any indicator of health, such as an ailment, a disease diagnosis, a condition related to health, details regarding insurance coverage, other information subject to regulation as personal health information. System 200 may next be acted on by consumer-database 204, where consumer-database 204 may activate function generate-keys 210. Function generate-keys 210 may use de-identification software that may sometimes be provided by healthcare-database 206 to generate keys corresponding to the individual consumers or households that are stored in consumer-database 204. Function generate-keys 210 may transmit the keys and a token of consumer information (for example, any or all of the name, address, phone number, Social Security number) to healthcare-database 206.

Healthcare-database 206 may invoke function correlate-keys-to-data 212, which may use the token of consumer information to attempt to match the key to the patient data in healthcare-database 206. Healthcare-database 206 may invoke function query-health-condition 214, which may use the health-condition preferences of user 202 to identify records in healthcare-database 206 that exhibit the specified health condition to answer the query of user 202. Healthcare-database 206 may invoke function sub-set-and-falsify 216, which may sub-set the answer to the query to remove data without statistically altering the outcome of the answer to the query of any given geographic region. Function sub-set-and-falsify 216 may also falsify a statistically insignificant amount of data in the answer to the query. Function sub-set-and-qualified (not shown) may take further actions to introduce uncertainty as to the probability of the health condition applying to any specific individual without statistically altering the answer to the query for any given geographic region.

Healthcare-database 206 may invoke function match-keys-and-health-expression 218, which may transmit the answer to the query (without any personally identifying information) and the associated keys to consumer-database 204. The answer to the query may be expressed as the key and an obscured expression of the health condition, which may be referred to as the health-expression herein. (See also FIG. 5B.) Consumer-database 204 may match the keys received in the answer from healthcare-database 206 to the keys stored in consumer-database 204 that were generated by function generate-keys 210. Consumer-database 204 may invoke function destroy-ID-info 220 to destroy the keys, consumer tokens, and any information or process used to help match the data received from healthcare-database 206 to the data in consumer-database 204. After destruction of this data, healthcare-database 206, using function un-obscure-health-condition 222, may transmit a map between the health-expression and the actual, descriptive health condition, which may be used by consumer-database 204. Consumer-database 204 may invoke function query-by-geography-and-consumer-demographics 224 to determine an answer needed to respond to a query from user 202 involving the previously selected health condition, geographic location, and other demographic data stored in consumer-database 204.

FIGS. 3A-3D show a data flow diagram illustrating the operation of an embodiment (system 300) involving transfer of data between healthcare-data entity 304 and consumer-data entity 302 while removing the information capable of identifying an individual. Note that the single lettered circles indicate connections between figures, and FIGS. 3A to 3D are considered together in the following text.

Figure 3A:
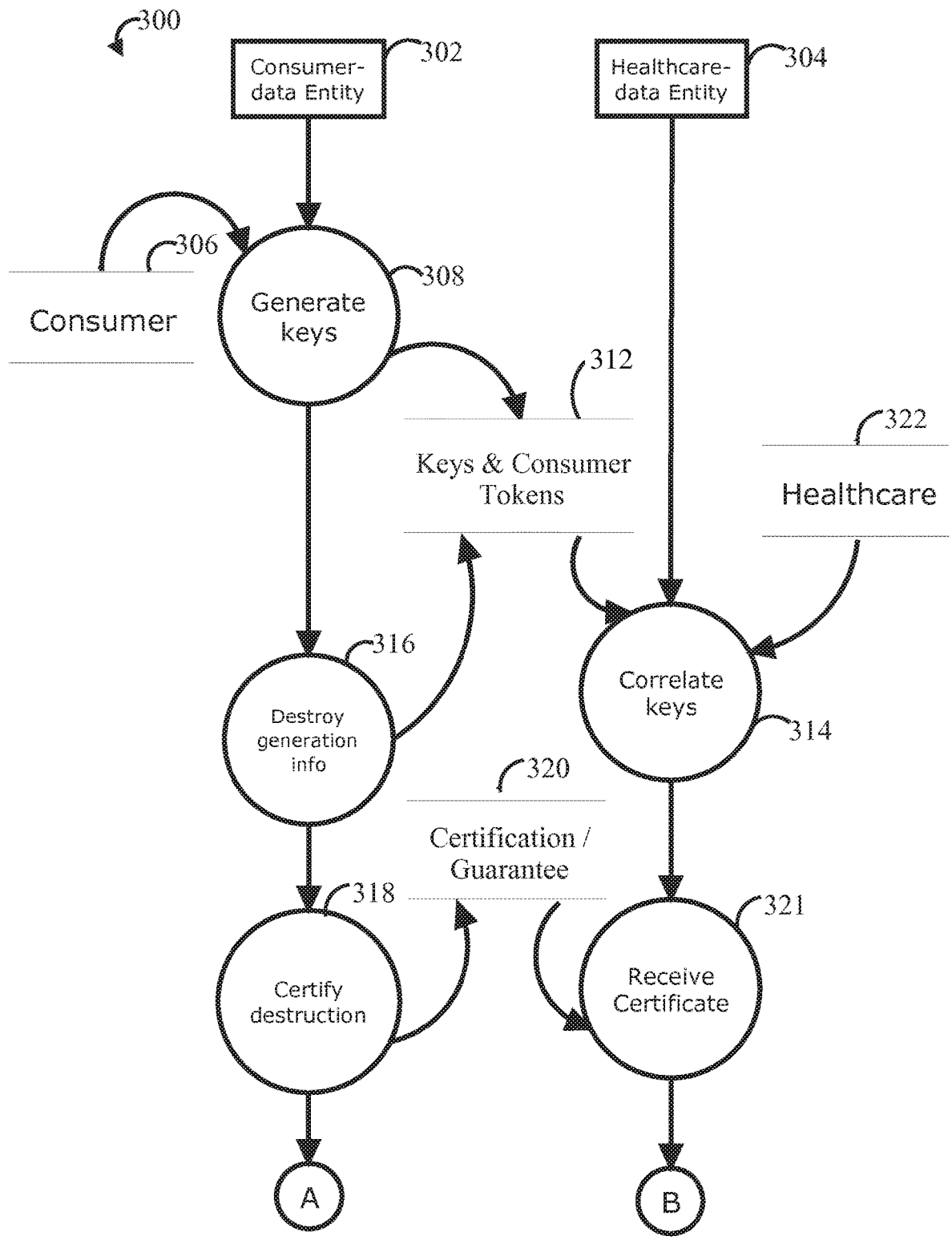
FIGS. 3A-3D show a data flow diagram illustrating an embodiment involving transfer of data between healthcare database entities and consumer database entities while removing the information capable of identifying an individual.

System 300 has a series of steps that may be performed by consumer-data entity 302 and healthcare-data entity 304, as shown in FIG. 3A. The term "entity" as used herein means a company, organization, or other entity that holds information such as a consumer or healthcare database. System 300 may begin by consumer database entity 302 performing the step generate-keys 308, which may query information from consumer database 306. Step generate-keys at 308 may use de-identification software to create a unique key for each record in consumer database 306. De-identification software may be any type of personal-information redactor or proxy system, such as, commercial de-identification software licensable from MedQuist or D-Id Data Corp. Step generate-keys 308 may store the key and a token of the consumer information into keys-and-consumer-tokens database 312.

Healthcare-data entity 304 may receive keys-and-consumer-tokens database 312 from consumer-data entity 302 and may perform step correlate-keys 314 using information from healthcare database 322. Step correlate-keys 314 may use the consumer information, such as name, address, phone, Social Security number, and other information that may identify a consumer, to match the keys in keys-and-consumer-tokens database 312 to the data for consumers stored in healthcare database 322; that is, step correlate-keys 314 tries to find the same person whose data is contained in consumer database 306 and match that person's data to corresponding data in healthcare database 322. The keys allow an association between the demographic information in consumer database 306 and the patient/healthcare information stored in healthcare database 322. However, because neither entity has physical, electronic, or any other access to the information of the other entity, additional regulatory requirements may not have been imposed upon either entity. That step may introduce additional risk of re-identification; consumer-data entity 302 may desire to mitigate that risk through statistically analyzing system 300 (including the process, steps, and data used therein) to recertify under such regulatory requirements. The references herein to regulatory requirements refer to any applicable governmental regulation, such as the Health Insurance Portability and Accountability Act ("HIPAA") or other requirements.

Step destroy-generation-info 316 may destroy the keys-and-consumer-tokens database 312 after transmitting keys-and-consumer-tokens database 312 to healthcare-data entity 304, so that only healthcare-data entity 304 has information relating the keys to the consumer tokens. Consumer-data entity 302 may retain only the keys in association with consumer database 306. Healthcare-data entity 304 may destroy keys-and-consumer-tokens database 312 after transmitting it to obscure-health-expression database 326 (see below). Electronic data destruction may be made irreversible by a variety of secure methods, such as physical or magnetic construction of electronic media or multiple rewriting of random data over electronic media.

Consumer-data entity 302 may perform step certify-destruction 318 by sending certificate-or-guarantee information 320 to healthcare-data entity 304, which will receive this information by step receive-certificate 321. Step certify-destruction 318 may require consumer-data entity 302 to take reasonable security measures to ensure that the appropriate information is destroyed, such as creating the key-and-consumer-tokens database 312 on computers physically and electronically separated from other networks or computers of consumer-data entity 302 or requiring that employees who perform these procedures or have access to the keys-and-consumer-tokens database 312 contractually, ethically, or otherwise promise to destroy the information or to keep the contents confidential from third-parties. These steps may or may not be required by law. These steps may be required by healthcare-data entity 304 or HIPAA statistician-or-auditor 360 because those entities may require the certification to perform other steps in the system such as step certify-process 358 (see FIG. 3D).

Figure 3B:
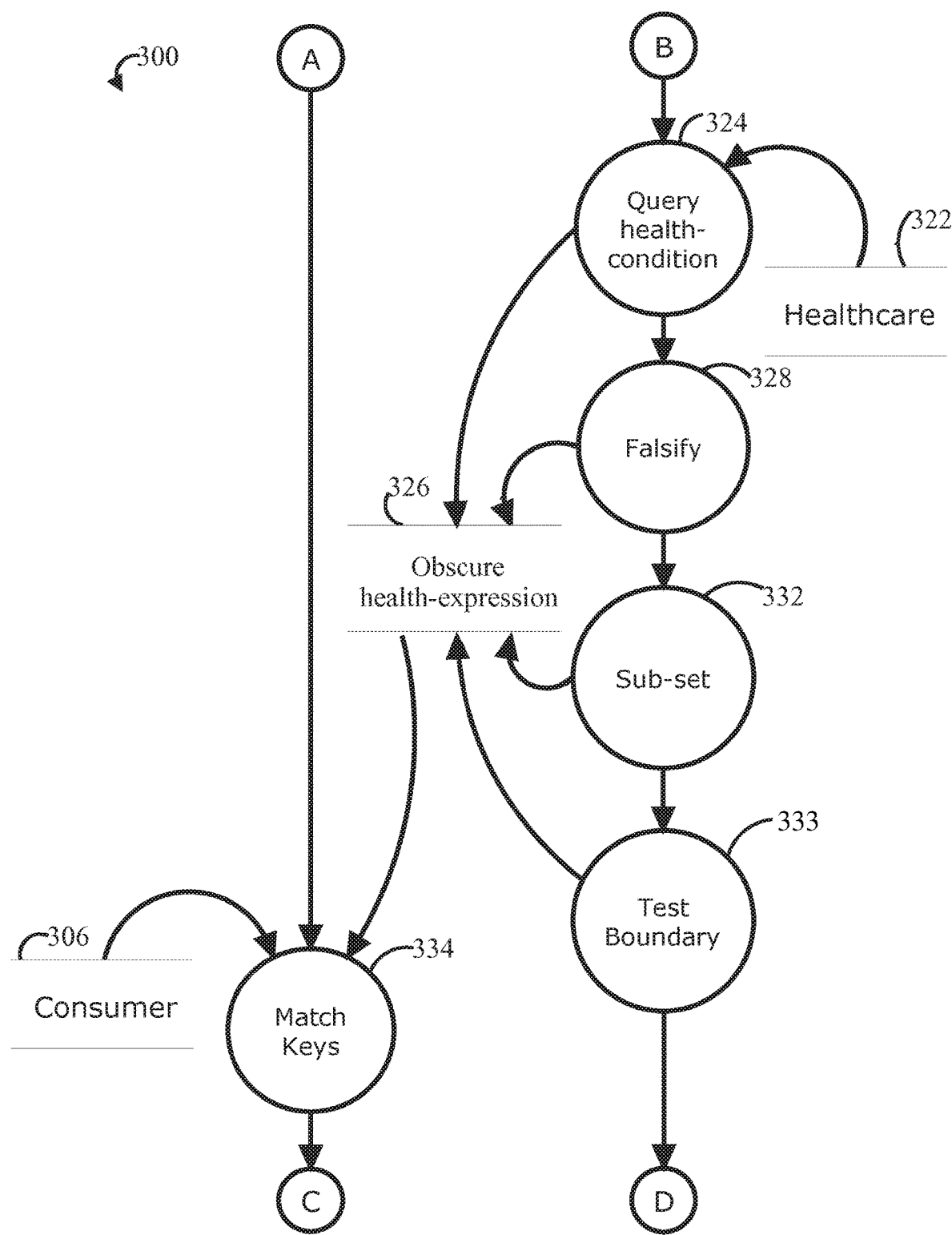

With reference to FIG. 3B, healthcare-data entity 304 may perform step query-health-condition 324. Step query-health-condition 324 may read the data from healthcare database 322 to determine the answer to a query regarding a specific health condition. Step query-health-condition 324 may begin storing this information in obscure-health-expression database 326 for eventual transmittal to consumer-data entity 302. The data stored in obscure-health-expression database 326 may be obscured so that consumer-data entity 302 may not learn the health condition of the individuals associated with the keys.

Step falsify-data 328 may add additional records to obscure-health-expression database 326, to create a statistically insignificant ambiguity in the data transmitted to consumer-data entity 302. By creating a statistically insignificant ambiguity, the usefulness of the data transmitted to consumer-data entity 302 is not diminished, because consumer-data entity 302 may use this data to determine only geographical regions that are suitable for targeting a message and not care to identify health concerns of specific individuals. That is, by introducing false information, even if someone attempted to re-identify the data transmitted to consumer-data entity 302, the result of that attempt would be suspect because false records would have been introduced. This may reduce the usefulness of the data transmitted to consumer-data entity 302 for determining health-condition of a particular individual. Alternatively, some geographical regions may be falsely selected or sub-settled to introduce further uncertainty in any effort by a third-part to re-identify the data, and such a situation may be acceptable because of the non-medical use of the data to transmit messages.

Healthcare-data entity 304 may perform step sub-set 332. Step sub-set 332 may remove records from obscure-health-expression database 326 to create a statistically insignificant ambiguity in the data transmitted to consumer-data entity 302. By creating a statistically insignificant ambiguity, the usefulness of the data transmitted to consumer-data entity 302 is not diminished, because consumer-data entity 302 may use the data to determine geographical regions and not care to identify health concerns of specific individuals. That is, by removing records, even if someone attempted to re-identify the data transmitted to consumer-data entity 302, the result of that attempt would be suspect because not all records would have been used. This may reduce the usefulness of the data transmitted to consumer-data entity 302 for determining health-condition of a particular individual.

Healthcare-data entity 304 may perform step test-boundary-condition 333. Step test-boundary-condition 333 may determine when a geographic region may exhibit characteristics that would allow consumer-data entity 302, or a third-party, to determine the health condition of an individual For example, if the health condition is arthritis and a particular Zip+4 postal code contained only a senior living facility where nearly all of the residents had arthritis, then the data transmitted to consumer-data entity 302 might be used to determine that a particular individual (all of the individuals) had the health condition of a diagnosis of arthritis. Likewise, for example, if a particular Zip+4 postal code contained only one African-American household, and the health condition is sickle cell anemia, the data transmitted to consumer-data entity 302 might be used to determine that that particular household contained an individual with sickle cell anemia. Under boundary conditions, where a very small number of individuals in a geographical region or all or almost all individuals in a geographical region exhibit the specified health condition, step test-boundary-condition 333 may exclude any data from a geographical region. Alternatively, the cooperation of the consumer-data entity 302 may be necessary to test and identify certain boundary conditions. Alternatively, certain querying of highly specific health conditions may not be permitted if such a query was likely to identify populations highly likely to exhibit boundary conditions.

Consumer-data entity 302 may perform the step of match-keys 334, by reading the information from consumer database 306 and using the keys to match the data in obscure-health-expression database 326 to each individual consumer's data in consumer database 306. Step match-keys 334 may store the health-expression, the keys, and the consumer data in a physically separated, electronically separated, or otherwise securely located system away from identifiable data or unauthorized employees to later aid step certify-destruction 342 (see FIG. 3C).

Figure 3C:
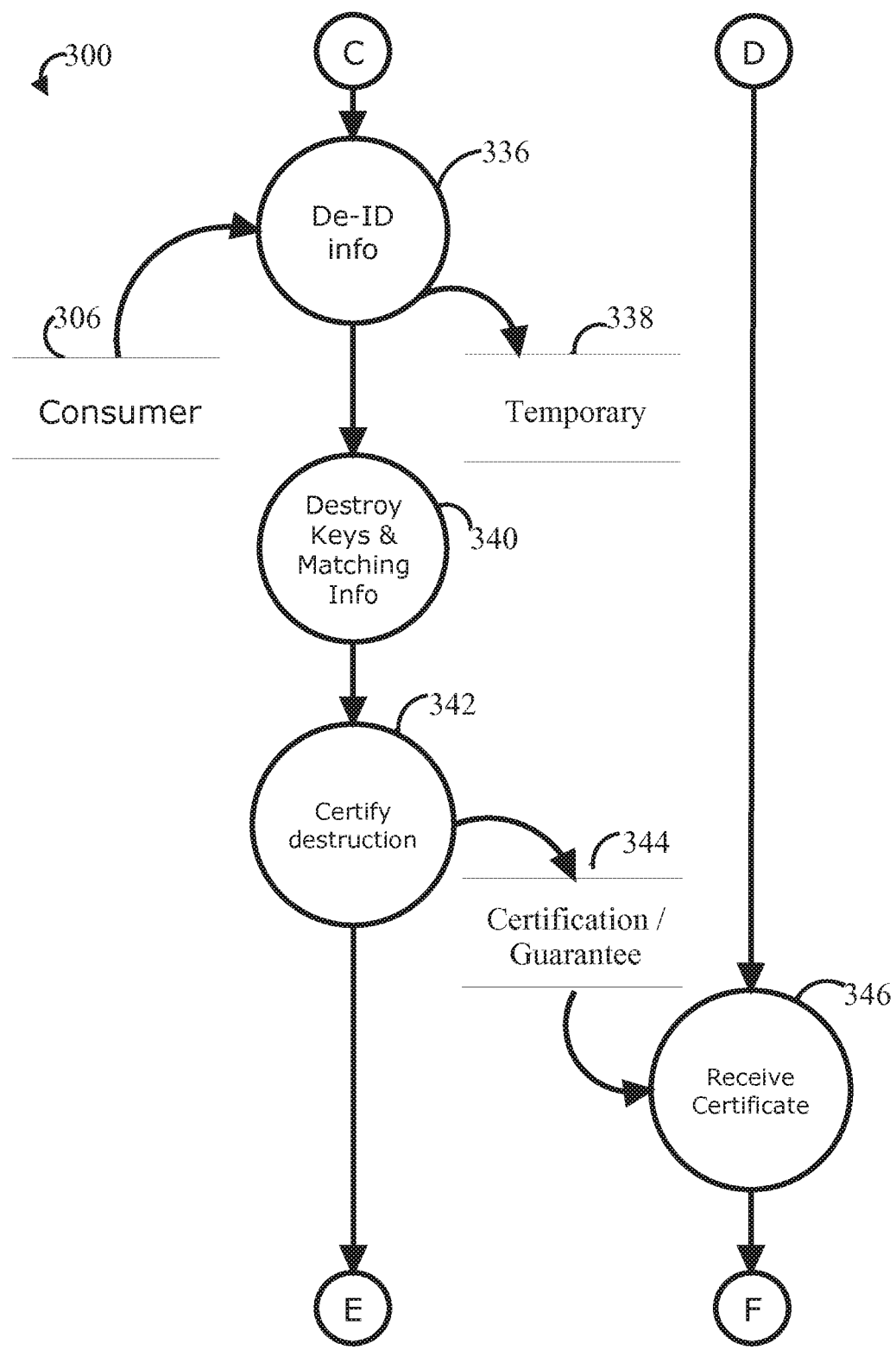

Consumer-data entity 302 may perform the step de-identify-info 336 by reading the consumer database 306 and writing geographical region information (such as a Zip+4 postal code), desired demographic information, the health-expression, and an aggregation of the number of consumers that indicate the health-expression into the temporary database 338, as shown in FIG. 3C. Temporary database 338 may be stored physically separated, electronically separated, or otherwise be securely located away from other data or unauthorized employees to later aid step certify-destruction 342.

Consumer-data entity 302 may perform step destroy-keys-and-matching-info 340 by destroying all traces of the keys, the process, temporary information, or any other physical or electronic records that may be able to link (or otherwise aid in the re-identification of) the information in the geo-health database 354 to the consumer database 306. Consumer-data entity 304 may perform the step of certify-destruction 342 by transmitting certification-or-guarantee information 344 to healthcare-data entity 304, which may receive the information by step receive-certificate 346. Similar to step 318, information 320, and step 321, these steps may be performed similarly to achieve similar objectives.

Figure 3D:
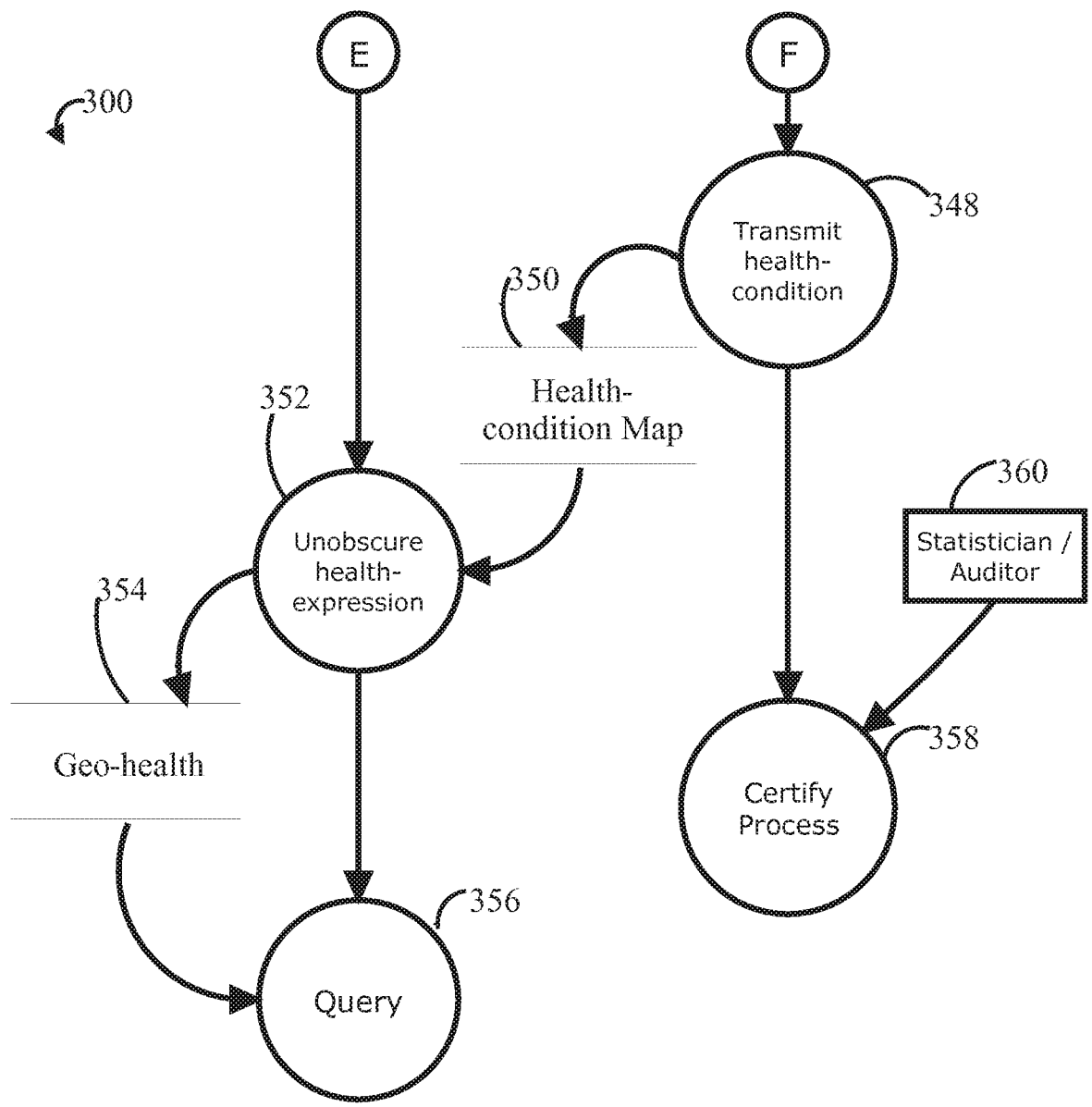

Healthcare-data entity 304, after being satisfied by the receipt of certificate-or-guarantee information 344, may perform step transmit-health-condition 348, as shown in FIG. 3D. Step transmit-health-condition 348 may write health-condition-map database 350, which may contain the health-expression and an indicator of the actual, descriptive health condition, so that the health-expression may be understood. Consumer-data entity 302 may perform the step of un-obscure-health-expression 352 by reading the transmitted health-condition-map 350 and associating the health-expression with the actual health condition. Step un-obscure-health-expression 352 may write to the geo-health database 354, which may contain a geographical indicator (for example, a Zip+4 postal code), demographic data, the health condition, and an indicator of the approximate quantity of individuals or households that exhibit the health condition.

Consumer-data entity 302 may perform step query 356 by querying information in the geo-health database 354 by using query parameters such as demographic profile information, geographical location, or a minimum quantity of households.

Healthcare-data entity 304 may perform the step certify-process 358 by allowing HIPAA statistician-auditor 360 to audit or to statistically ascertain that system 300 complies with governmental regulations that require privacy of individual's personal health information, such as HIPAA. System 300 may further allow compliance with other types of regulations, such as compliance with company privacy policy (which may be stricter than governmental regulation), or other laws. System 300 may be statistically certifiable as compliant with government regulations restricting the use of personal health information (for example, HIPAA) because: healthcare-data entity 304 never has access to the data of consumer-data entity 302 and consumer-data entity 302 never has access to the data of healthcare-data entity 304 (except the health-expression, which is meaningless before step un-obscure-health-expression 352 is performed), or consumer-data entity 302 may not know the meaning of the health expression whenever it is working with identifiable data. Further, limiting the quantity of data sent (for example, using a two-valued health-expression as discussed in FIGS. 5B and 5C) and obscuring the description of the health condition may further assist the statistical process of certification for compliance with laws restricting the use of personally identifiable health information.

Upon reading the teachings of this specification, those with ordinary skill in the art will realize that, under appropriate circumstances, considering such issues as technology preference, system architecture, security, economic considerations, advances in technology, and user preference, other types of databases, such as flat files, XML, HTML, CSV files, database exports, text files, EDI, or other file types, and other transmission protocols, may suffice.

Figure 4:
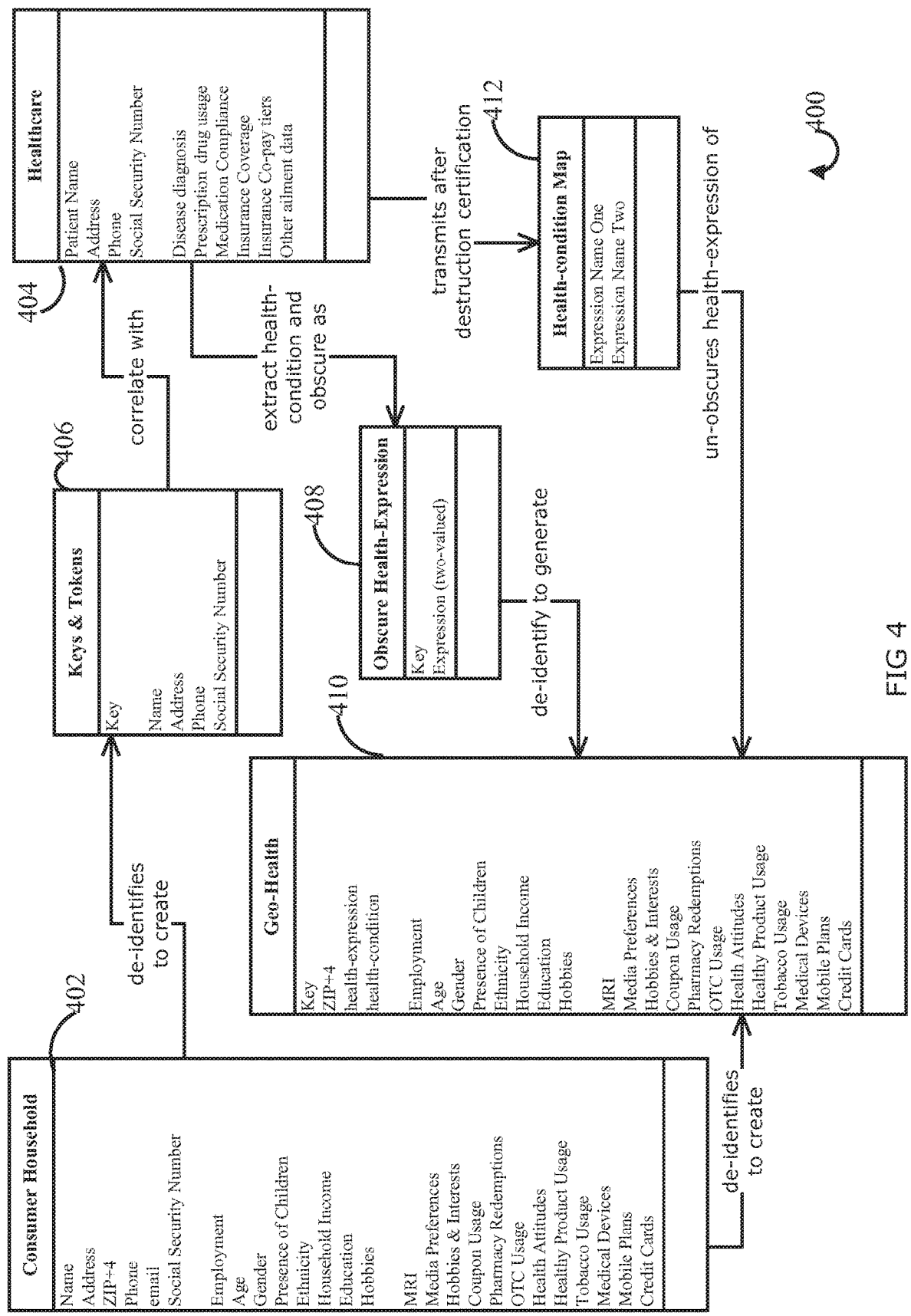
FIG. 4 shows a class diagram illustrating the relationships among healthcare database objects, consumer database objects, and other example objects, including examples of attributes, according to an embodiment.

FIG. 4 shows a class diagram illustrating the relationships between healthcare database objects and consumer database objects and other example objects, including examples of attributes, according to an embodiment.

System 400 shows objects and their relationships to each other. Object consumer-household 402 shows some example attributes that may be stored for consumer household postal information by a consumer-data entity. Object consumer-household 402 may contain information related to contacting or identifying the consumer such as name, address, Zip+4, phone number, e-mail address, and Social Security number. Object consumer-household 402 may contain information obtained during the U.S. Census such as employment, age, gender, presence of children, ethnicity, household income, education, and hobbies. Object consumer-household 402 may contain information from credit reporting agencies such as Equifax, TransUnion, or Experian. Object consumer-household 402 may contain information from consumer surveys (for example, self-reported consumer surveys) such as MRI, Simmons' Attributes, media preferences, hobbies and interests, coupon usage, pharmacy redemptions, OTC usage, health attitudes, health product usage, tobacco usage, medical device usage, mobile plans, and credit card data. Object consumer-household 402 may contain only information that may not be subject to governmental regulation because the information would not be considered personal health information.

Object consumer-household 402 may be related to object keys-and-tokens 406 because object consumer-household 402 may be de-identified to create the object keys-and-tokens 406. Object consumer-household 402 may be related to object geo-health 410 because object consumer-household 402 may be de-identified to create the object geo-health 410.

Object healthcare 404 shows some example attributes that may be stored for a patient by a healthcare-data entity. Object healthcare 404 may contain information used to identify the patient such as patient name, address, phone, and Social Security number Object healthcare 404 may contain personally identifiable health information that usually is the subject of governmental regulation (for example, HIPAA). Object healthcare 404 may contain information used to record medical treatments or medical billing such as disease diagnosis, prescription drug usage, medical compliance, insurance coverage, insurance co-pay tiers, and other ailment data Object healthcare 404 may be related to object obscure-health-expression 408 because object healthcare 404 may extract a portion of its information and obscure that information to create object obscure-health-expression 408. Object healthcare 404 may be related to object health-condition-map 412 because object healthcare 404 may generate for later transmission object health-condition-map 412 whenever object obscure-health-expression 408 is generated. Object obscure-health-expression 408 may contain aggregated, de-identified health insurance claims from pharmacies, physicians, hospitals, insurers, or other medical providers.

Object keys-and-tokens 406 may contain information used to relate a consumer's demographic data to the consumer's healthcare data using a unique and non-identifying key. Object keys-and-tokens 406 may contain tokens of information useful or helpful to ensure that the same consumer is identified in object consumer-household 402 and object healthcare 404. In an alternate embodiment, the tokens of information may not be supplied; rather, the same software may be used by the healthcare-data entity and the consumer-data entity, and that de-identification software may be designed to always generate the same key given similar consumer identification information. Exact mapping between consumers in object consumer-household 402 and object healthcare 404 may not be required to effectively model the geographical areas that are subject to the health condition or other term of the query. Object keys-and-tokens 406 may be related to object healthcare 404 because the keys or tokens of object keys-and-tokens 406 may be used to correlate with object healthcare 404.

Object obscure-health-expression 408 may contain information and attributes used to create object geo-health 410 by de-identifying consumer-household 402, as shown. Object obscure-health-expression 408 may contain the unique key and a health-expression. Each health-expression may be two valued, such as "yes" or "no", zero (0) or one (1), or "T" or "F". Limiting the amount of information that is encoded in health-expression reduces the risk that the consumer-data entity or a third party may be able to re-identify the data.

Object geo-health 410 may contain information or attributes that relate the demographic information from object consumer-household 402 to a geographic identifier, such as Zip+4, and to the health-expression, and later, to the health condition. Object health-condition-map 412 may contain information and attributes used to map the obscure health-expression to the actual health condition. Object health-condition-map 412 may contain two attributes that describe the two values of the health-expression.

Upon reading the teachings of this specification, those with ordinary skill in the art will realize that, under appropriate circumstances, considering such issues as security, encryption, governmental regulations, economic considerations, advances in technology, and user preference, other types of obscuring or health-expressions, such as three-valued, multi-valued, or encrypted health-expressions, or other methods of obfuscation or obscuring health conditions, may suffice.

FIGS. 5A-5C show data structure layouts illustrating example values of data transmitted between the consumer household database and the healthcare database, according to an embodiment.

FIG. 5A shows a table illustrating a data structure layout for a keys-and-tokens data file (such as object keys-and-tokens 406). The columns include the unique key, the name, the address, the phone number, and the Social Security number. Alternatively, other kinds of identifying information could be used such as e-mail addresses, fax numbers, previous addresses, or employment records. The key may be uniquely generated. The key may be random or sequential. The key may not embody, encrypt, or otherwise identify the consumer.

FIG. 5B shows a table illustrating a data structure layout for an obscure-health-expression data file (such as object obscure-health-expression 408). The columns include the key and the health-expression. In this embodiment, the key is uniquely generated and relates to FIG. 5A. The health-expression may be zero or one.

FIG. 5C shows a table illustrating a data structure layout for a health-condition map data file (such as object health-condition-map 412). The columns include the health condition and the health-expression. In this example, the health-expression indicated by "0" is mapped to the health-condition description "positive for arthritis and NSAID treatment." In this example, the health-expression indicated by "1" is mapped to the health-condition description "negative for arthritis and NSAID treatment." As discussed above, other methods of obscuring the health condition may be used.

Figure 6:
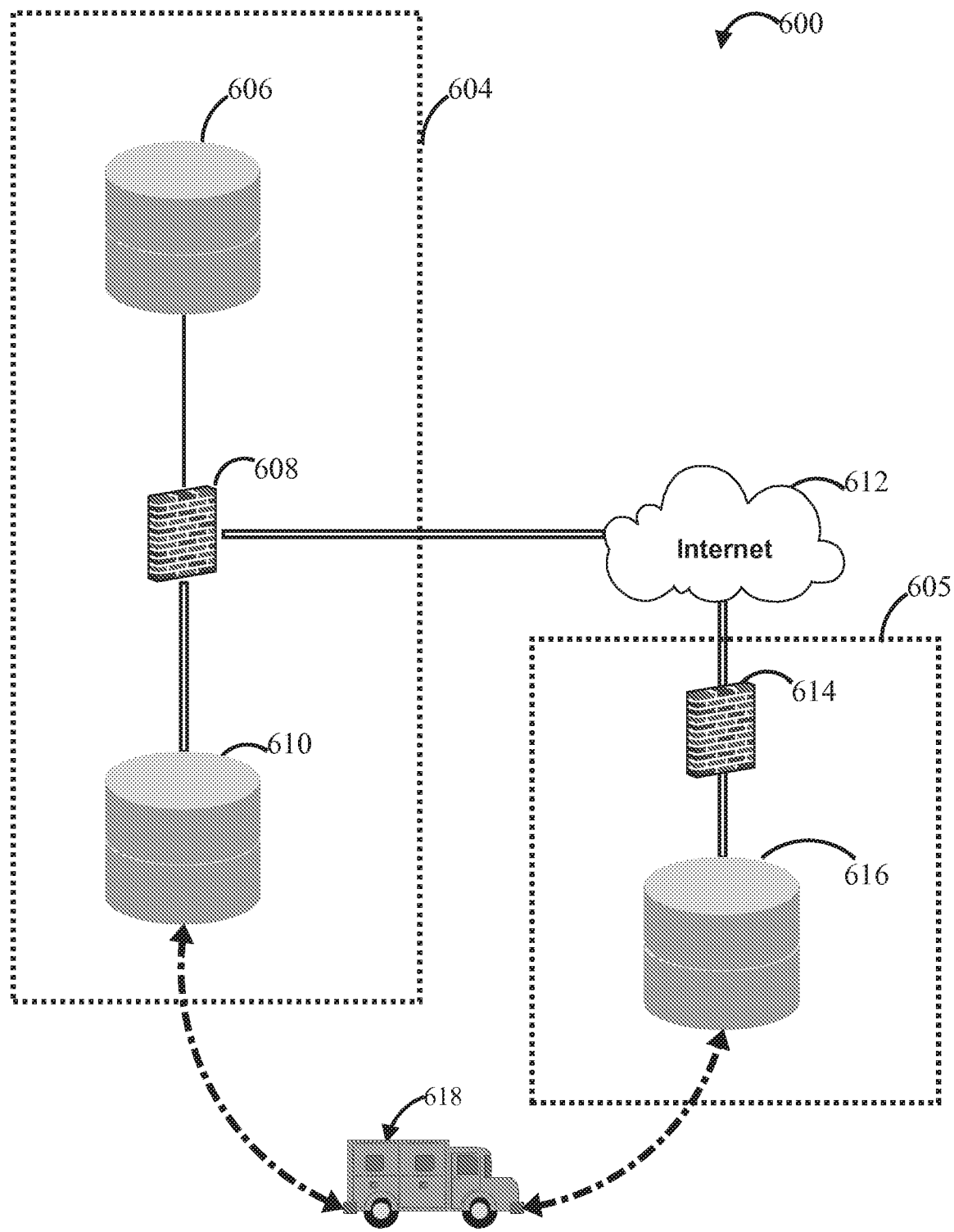
FIG. 6 shows a network architecture diagram illustrating a computer system configured to perform the steps of securely transferring information by secure physical delivery or by secure transmission over an insecure network, according to an embodiment.

FIG. 6 shows a network architecture diagram illustrating computer system 600 configured to perform the steps of securely transferring information by an insecure network (by encryption or secure channel) or secure physical delivery according to an embodiment. System 600 includes consumer-data entity 604 and healthcare-data entity 605. Consumer-data entity 604 may store consumer household demographic data on consumer household postal database 606. Consumer-data entity 604 may generate keys and tokens for transmittal to healthcare-data entity 605. Consumer-data entity 604 may use secure geo-health database 610 to create keys and tokens, which may be physically or electronically secured or otherwise separated from consumer-data postal database 606 by security-measures 608. Security-measures 608 may include network firewalls, security systems, security cameras, nondisclosure agreements, and other protective measures to ensure that the information stored on geo-health database 610 remains confidential and is not transmitted to unauthorized third parties. Security-measures 608 may include a dedicated computing platform (that is, physically and or electronically separated from other systems), on-site security, software destruction programs, preventing access by third parties, etc.

After generation of keys and tokens, consumer-data entity 604 may transmit the keys and tokens to healthcare-data entity 605 over an insecure network, such as the Internet 612 (or other global or computer network). Consumer-data entity 604 may transmit the keys and tokens using an encrypted or otherwise secure channel such as secure socket layer, SFTP, FTPS, SSH, SCP, or virtual private network (VPN). Healthcare-data entity 605 receives the keys and tokens into healthcare database 616 through security measures 614. Alternatively, data may be transmitted using a secure private line or private network or similar private connection.

Alternatively, consumer-data and the 604 may transmit the keys and tokens to healthcare-data entity 605 using physical media such as tape (capable of recording electrical signals), or a CD-ROM. The physical media may be transmitted by courier 618. Ultimately, other methods of transmitting the data without revealing the contents of the key and token information to third parties may be used.

FIGS. 7A and 7B show data structure layouts illustrating example values of data files to identify consumers or geographical areas to automatically transmit messages that correspond to selected health conditions and selected demographic conditions, according to an embodiment.

FIG. 7A shows a table illustrating a data structure layout for a list of consumers that live in a geographical area specified by a query including a selected health condition and a selected demographic condition. This table may contain personal information, such as mailing addresses, phone numbers, or e-mail addresses, which may be used to automatically contact the individuals or households.

FIG. 7B shows a table illustrating a data structure layout for a list of geographical areas that were specified by a query including a selected health condition and a selected demographic condition. This table may contain Zip+4 information and a percentage of the individuals and households that exhibit a selected demographic condition and selected health condition. This table may also contain Internet protocol ("IP") address ranges that are typically assigned to a geographical area. The Zip+4 information may be used for direct mail, email, addressable advertising by cable TV operators or by magazine and newspaper publishers, and any other type of addressable messaging. The IP address ranges may be used for targeted online messages. This table may also contain latitude and longitude locations that directly indicate the geographical area that may be used when GPS information is available to the automated message delivery system. Alternatively, a simple list of Zip+4 codes that meet the selected demographic condition and selected health condition may be provided to further ensure the privacy and irreversibility of the healthcare information used to generate this data. Alternatively, a list using geographic proper names, such as cities, towns, subdivisions, or streets, may be used to determine geographic areas that meet the selected health condition and demographic profile.

Figure 8:
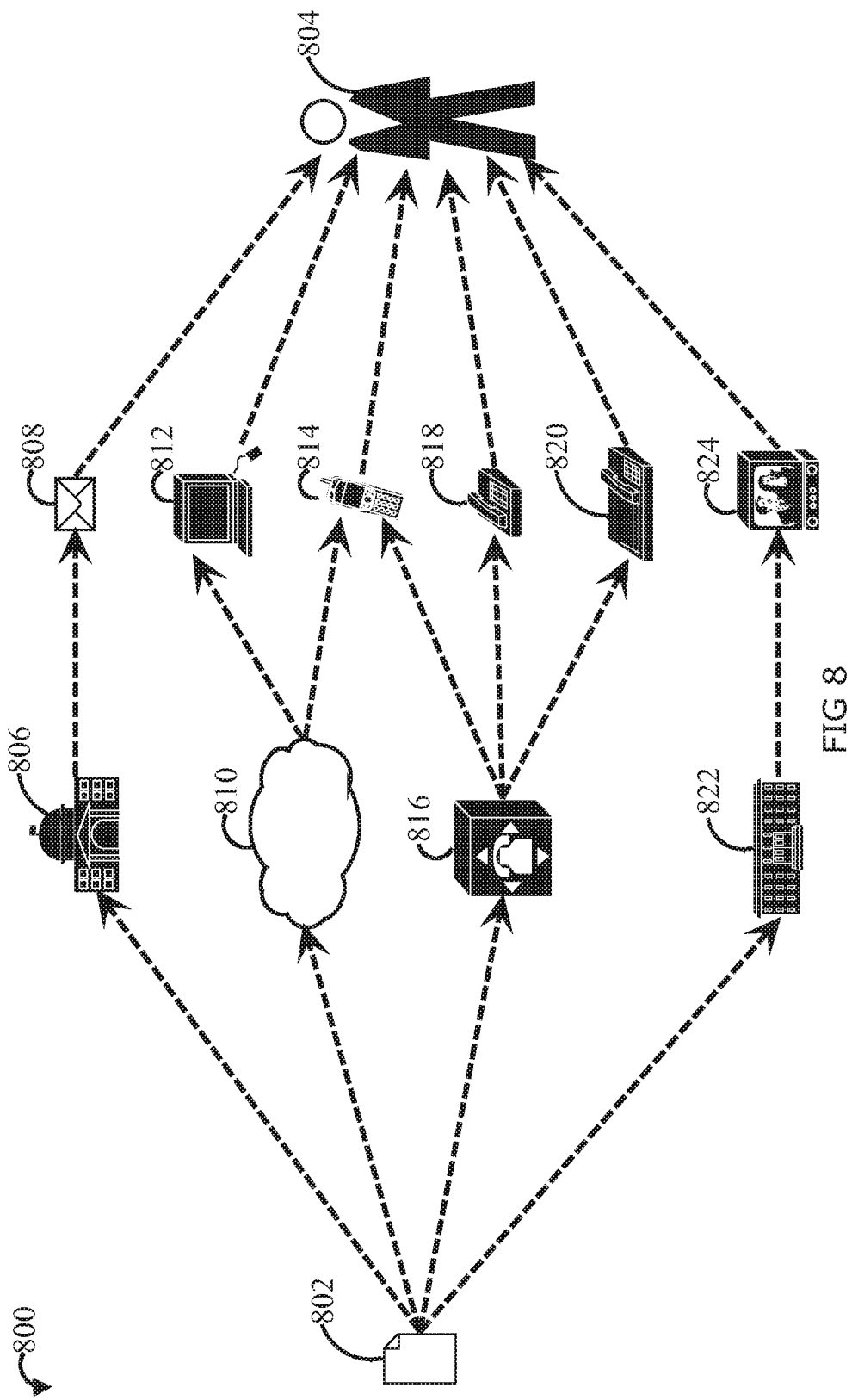
FIG. 8 shows a system architecture diagram illustrating various computer systems for distributing documents and messages to target specific geographic locations with a propensity for a specific health condition and specific demographic profile, according to an embodiment.

FIG. 8 shows a system architecture diagram illustrating various automated systems for distributing documents and automated messages to target specific geographic locations with a propensity for a specific health condition and a specific demographic profile, according to an embodiment.

Automated delivery systems 800 may include methods to transmit message 802 to consumer 804. Automated delivery systems 800 include delivery methods such as postal delivery 806, computer network 810, telephone network 816, and television network 822.

Postal delivery 806 may transmit message 802 by various mail pieces 808. Mail pieces 808 may include direct mail for delivery to the geographic areas (list of ZIP+4) that correspond to a specified health condition and specified demographic profile. Mail pieces 808 may be directed by segmenting a portion of all copies of a nationally distributed publication, requesting a printing of those copies including with message 802 included, and delivering those copies to the geographic areas (list of Zip+4 areas) that correspond to a specified health condition and specified demographic profile.

Computer network 810 may transmit message 802 by methods including using the geographic area (for example, the Zip+4) and an IP address or email address (which may be used by mapping the IP or email address to a Zip+4 or to the geographic area directly). Computer network 810 may facilitate transmittal for cost per click ("CPC") or pay per click ("PPC") advertising by using either Zip+4 lists, IP address lists, or email address lists; the list may be selected based on economic considerations, technological advances, or other factors concerning the targeted delivery of message 802. Computer network 810 may transmit messages to computer 812, which may display CPC, PPC, banner advertising, or other Internet- or network-based advertising capable of distinguishing what message to display based on email, IP, network address, or other online identifier. Computer network 810 may deliver messages to handheld device 814. Handheld device 814 may be a mobile phone or personal data assistant ("PDA") capable of transmitting information over computer network 810. Handheld device 814 may be capable of transmitting the GPS location (that is, the latitude and longitude) of the individual. Computer network 810 may use the GPS location to determine if message 802 should be sent to handheld device 814. Computer network 810 may be able to transmit message 802 to handheld device 814 using voice over IP ("VOIP") protocol, when message 802 is a prerecorded audio message. Computer network 810 may be able to transmit message 802 to computer 812 and handheld device 814 as an e-mail message.

Telephone network 816 may transmit message 802 to telephone 818 and handheld device 814 (when handheld device 814 is a mobile phone or other device capable of receiving information via telephone network 816), whenever message 802 is a prerecorded audio message, such as by using an automated dialer. Telephone network 816 may transmit SMS text messages to mobile phones (that may be owned by individuals living in a selected geographic area), which messages allow the user to respond and listen to a prerecorded message. Telephone network 816 may transmit message 802 to fax machine 820, whenever message 802 is an electronic fax transmission.

Television network 822 may transmit message 802 to television 824, whenever message 802 may be targeted to a specific geographic area and may be within the cable operator's jurisdiction. For example, cable television operators can transmit different television signals to different geographic locations on the same channel. This may allow message 802 to be delivered only to geographic areas that have a high correspondence to the specified health condition and specified demographic information. Television network 822 may transmit message 802 to consumer 804 using addressable TV technology, such as digital cable TV.

Upon reading the teachings of this specification, those with ordinary skill in the art will realize that, under appropriate circumstances, considering such issues as technology preference, system architecture, delivery method, media, message content, economic considerations, advances in technology, and user preference, other types of automated messages, such as radio commercials, television commercials, text messages, instant messages, SMS messages, and social networking advertising, other transmission protocols, and other ad campaign techniques, such as opt-in/opt-out email, opt-in/opt-out direct mail, consumer publications, local newspapers, consumer portals, cell phone browsers, direct response TV, clinical trial patient recruiting, or CRM appends may suffice.

Figure 9A:
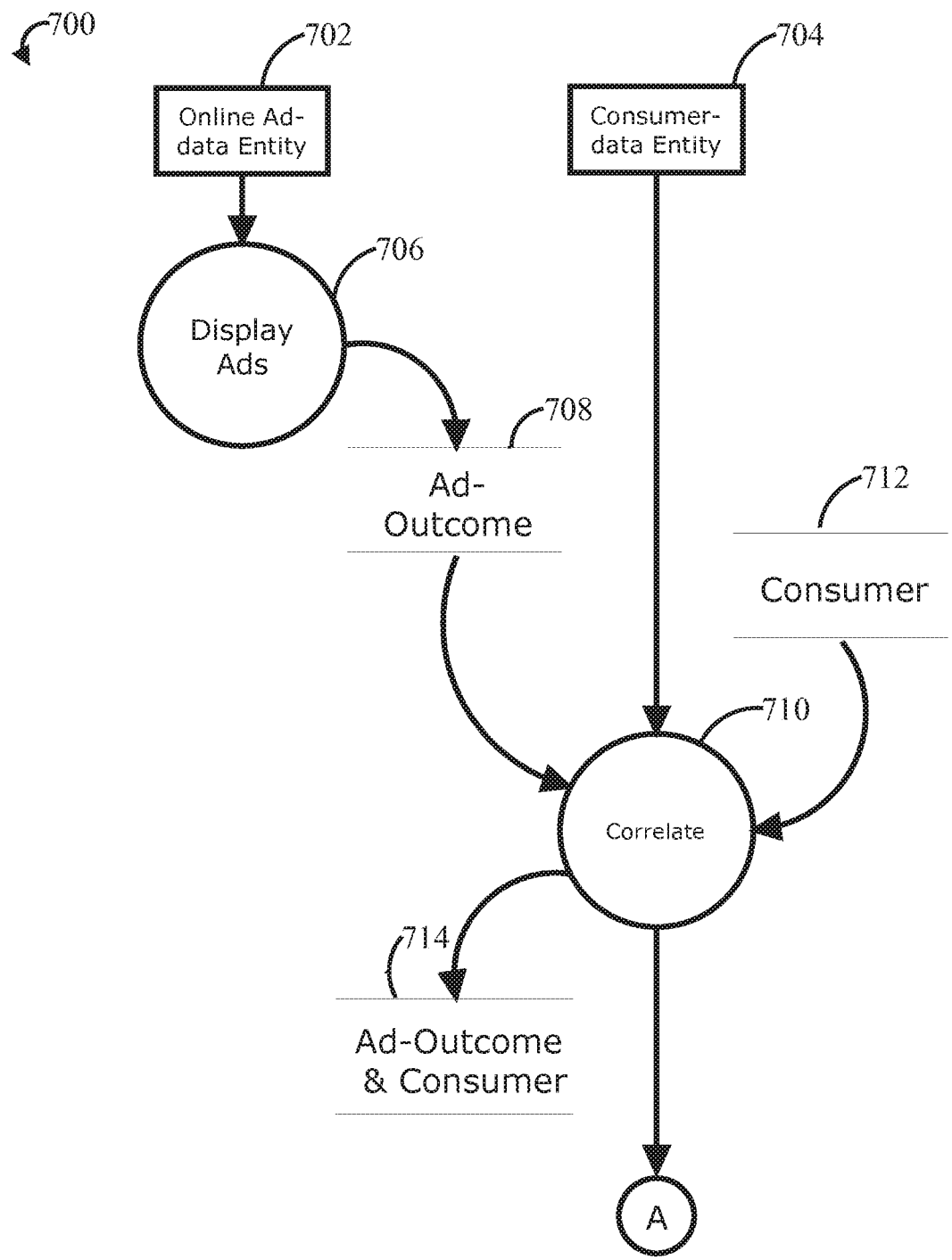
FIGS. 9A-9C show a data flow diagram illustrating a series of steps to measure the effect of an online advertising campaign, according to an embodiment.
Figure 9B:
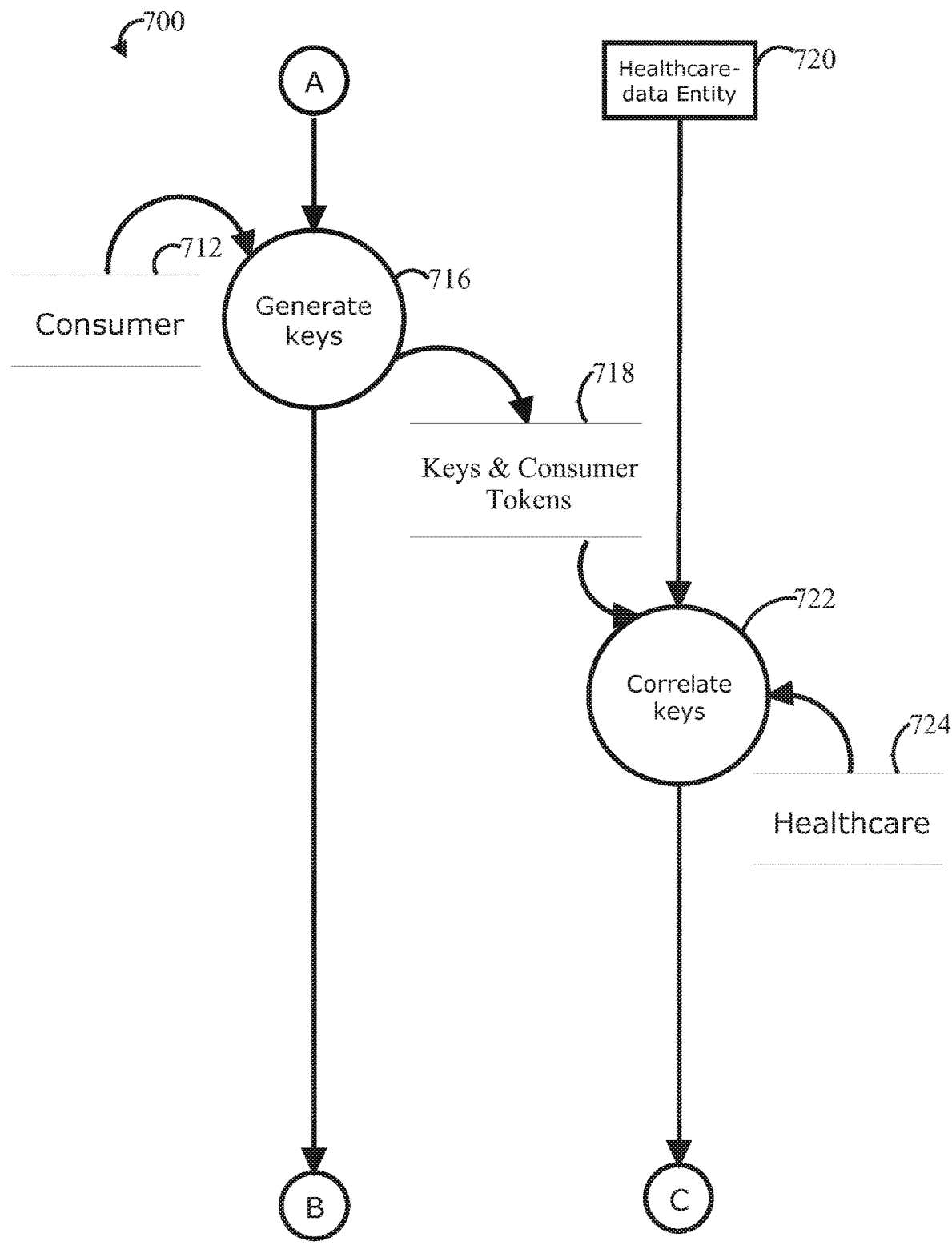
Figure 9C:
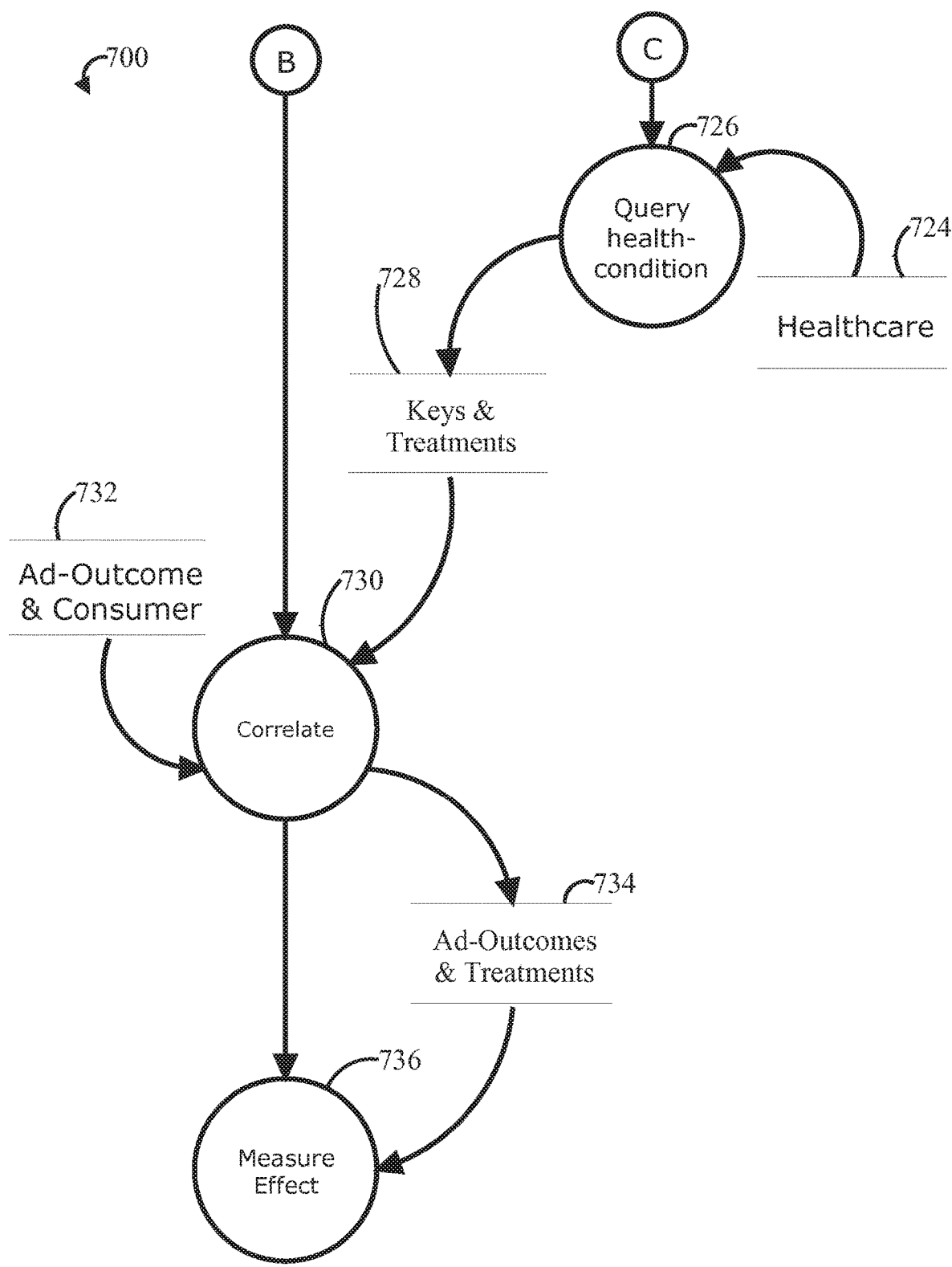

FIGS. 9A-9C show a data flow diagram illustrating a series of steps of system 700 to measure the effect of an online advertising campaign, according to an embodiment. In this embodiment, the foregoing methods can be applied to determine the effectiveness of online advertising, for example by allowing calculation of a return on advertising investment for advertising programs that are disseminated online, typically through a globally connected network such as the Internet. Note that the single-lettered circles indicate connections between figures, and FIGS. 9A-9Cc, which are considered together in the following discussion.

In embodiments that measure the impact of digital display advertising, medical record information, consumer information, and Internet Protocol address information are merged and evaluated to aid analysis of online advertising. Analysis may include the effectiveness of the targeting of the online advertising, the relevance of the message used in the online advertising, and whether the results of the online advertising may be statically proven. The analysis may be used to vary future advertising media mix, for example by using more or less online advertising in comparison to other media (TV, radio, print, etc.) The analysis may be used to compare various online campaigns to one another. The analysis may be used to determine if targeting specific consumers or health condition sufferers may achieve a specified performance level. Personally identifiable consumer data may be excluded from viewing or analysis, which may allow HIPAA-certification of the process or entities by a statistician, who may be independent from the other entities discussed in FIG. 9.

System 700 and may perform a series of steps by online ad data entity 702, consumer-data entity 704, and healthcare data entity 720, as shown in FIG. 9A. System 700 may calculate a return on advertising investment to help show what effect an online advertising campaign may have for products or services related to a treatment for an ailment. System 700 may be able to calculate a return on advertising investment even after the conclusion of the online advertising campaign.

System 700 may begin with the online ad data entity 702 performing step display-ads 706. Step display-ads 706 may display advertisements that may be related to a particular treatment for an ailment. Step display-ads 706 may generally capture an online identifier to indicate to whom the advertisement was displayed, for example an advertisement may be displayed to a particular Internet protocol address or sent to a particular e-mail address. Step display-ads 706 may display advertisements by paying for inclusion in search engine results, for example paid search. Step display-ads 706 may display advertisements on social media websites. Upon reading the teachings of the specification, those with ordinary skill in the art will realize that, under appropriate circumstances, considering such issues as technology preference, system architecture, delivery method, advertising content, economic considerations, advances in technology, user preferences, and media, other types of online identifiers may suffice.

Step display-ads 706 may store the online identifier in the ad-outcome database 708. Step display-ads 706 may also store the result or outcome of the advertising display to the particular user, such as whether the user only viewed the ad, whether the user clicked the ad, or whether the user redeemed the ad. For the purpose of this specification, redeeming an advertisement means any action a user takes in response to an advertisement that may be tracked by the online ad-data entity 702, such as allowing the user to sign up for newsletter, allowing the user to sign up for additional information, providing the user with a coupon, or otherwise capturing information about the user. Step display-ads 706 may write a "cookie" to the web browser of the user to whom the ad is displayed, to track additional usage or repeated view by the same user or same web browser, which may allow tracking of progress through other websites where the same web advertising server is used to display ads. The ad outcomes collected during the display of online advertising may include IP addresses that were exposed to online advertising, the IP address that clicked through the online advertising, and IP addresses that "opted-in," converted, or redeemed the online advertising.

Ad-outcome database 708 may store any information about the displaying of advertisements. Ad-outcome database 708 may contain online advertising outcomes for online advertisements related to a health condition that is a set of online-advertising-outcome data.

Consumer-data entity 704 may begin by correlating the ad-outcome database 708 to the consumer database 712. To correlate the set of online advertising outcome data to the set of consumer data, the online identifier may be used. To correlate the ad-outcome database 708 to the consumer database 712, step correlate 710 may match information in the ad-outcome database 708 to information in the consumer database 712. In one embodiment, the correlated information may include the Internet protocol address. In another embodiment, the correlated information may include the e-mail address. When an advertisement is redeemed, other information may be available to help correlate, such as first and last names, street addresses, telephone numbers, or additional e-mail addresses. It may not be necessary to correlate every record of ad-outcome database 708 to a record in consumer database 712 because to calculate a return on advertising investment with sufficient statistical certainty, not every record may be required. Step correlate 710 may store the combination of the ad-outcome database 708 and the consumer database 712 in ad-outcome and consumer database 714.

Consumer-data entity 704 may continue with step generate-keys 716, as shown in FIG. 9B. Step generate-keys 716 may be performed similarly to step generate-keys 308 as discussed above in reference to FIG. 3A. Step generate-keys 716 may use consumer database 712 to generate keys and consumer tokens (for example, by de-identification, as previously discussed in connection with FIG. 3A and elsewhere) for keys and consumer tokens database 718. Cost may be a factor in selecting the details of the de-identification process; for example, de-identification to determine a ZIP+4 may cost less than de-identification to determine a particular individual or a particular household. Other steps in the de-identification process may be included as desired to protect the privacy of the individuals, for example falsification of a portion of the healthcare claims database or selecting ZIP+4 level rather than individual or household level. Transmission of de-identified data, including keys and consumer tokens may be handled by secure transmission.

Healthcare-data entity 720 may use keys and consumer tokens database 718 for step correlate keys 722 to correlate with healthcare database 724. Step correlate-keys 722 may be performed similarly to step correlate-keys 314, as discussed above in reference to FIG. 3A. Healthcare-data entity 720 may continue with step query-health-condition 726, as shown in FIG. 9C. Step query-health-condition 726 queries healthcare database 724 for records related to the health condition or ailment that is the subject matter of the online advertising. Step query-health-condition 726 may determine what treatment or change in treatment (or other change in healthcare information that may be quantified) occurred during the same time period as the online advertising or can otherwise be linked to the display of the online advertising. Healthcare claims data that matches the de-identified patients or consumers may be found to determine what treatments (or new diagnosis) may have been attributable to the display of the online advertisement.

Step query-health-condition 726 may return records related to the keys and consumer tokens database 718 and records that are not related to the keys and consumer tokens database 718 but are related to the health condition targeted by the online advertising. Step query-health-condition 726 may query healthcare database 724 using the health condition targeted by the online advertising to determine treatments provided to patients. Step query-health-condition 726 may query healthcare database 724 to establish any relationship to the online advertising outcome. In an embodiment, records related to consumers viewing advertising may eventually form part of a test group, and records not related to consumers viewing advertising may form part of a control group. By comparing the test group to the control group, step query-health-condition 726 may determine variations in the quantity of treatment between the two groups, which may be statistically analyzed. In another embodiment, only records related to consumers viewing advertising may be returned. Step query-health-condition 726 may supply keys-and-treatments database 728 with treatment information from health care database 724 in relation to the keys from keys and consumer tokens database 718. In some embodiments, treatment information may be summarized by geographical region, such as the ZIP+4 area. In other embodiments, treatment information may be grouped by online-identifier.

Treatment information may be quantized for analysis, for example by summing the new prescription activity for a drug featured in an online advertisement or summing the refill prescription activity for a drug featured in an online advertisement.

Consumer-data entity 704 may perform step correlate 730. Step correlate 730 may associate keys-and-treatments database 728 with ad-outcome-and-consumer database 732. This step allows association of the online-identifier with the summarized treatment information in the keys-and-treatments database 728. This step may write to add-outcomes-and-treatments database 734. As discussed previously, step correlate 730 (or other steps as necessary) may include steps to destroy any information capable of identifying any individual (while retaining information that allows relationship to the IP address that is serving as a geographical location) whose healthcare information may be stored in healthcare database 724. As discussed previously, step correlate 730 (or other steps as necessary) may include steps to certifying the step of destroying, to guarantee that the consumer data may not be used to identify the health-condition of any individual. As discussed previously, step correlate 730 (or other steps as necessary) may include certification of the system by a statistical professional that the system complies with governmental regulation of personal healthcare information.

Consumer-data entity 704 may perform step measure effect 736. Step measure effect 736 may calculate the return on investment for advertising dollars by calculating the difference in treatment of the test group that was exposed to the online advertising to the increase in treatment of the control group that was not exposed to the online advertising. Statistically, both groups may be equally likely to be exposed to mass-media advertising, for example television commercials, radio commercials, or direct mail. By dividing the set of healthcare data into at least two groups and comparing a group exposed to the online advertising and a group not exposed to online advertising, the process may assist in determining the effectiveness of the online advertising. In some embodiments, calculations may be done for a series of periods, for example week over week, month over month, or day over day. In some embodiments, calculations may compare periods before and after online advertising. By dividing the groups by time periods and comparing before and after the period of online advertising, the process may determine the effectiveness of the online advertising. This may allow step measure effect 736 to compare the amount spent on online advertising to the difference between the amount of treatment for the group exposed and the amount of treatment for the group not exposed, which may allow a calculation of the return on investment.

In another embodiment, step measure effect 736 may instead compare the effectiveness of one online advertising campaign with another online advertising campaign in order to compare the relative effectiveness of the online advertising campaigns, for example to determine the most effective online advertising campaign. In this embodiment, the quantity of treatment arising after the first advertising campaign may be compared to the quantity of treatment arising after the second advertising campaign. The quantity of treatment may be adjusted proportional to the number of times that the advertisement was displayed. For example, a quotient may be calculated of the total quantity of treatment results for the first advertising campaign divided by the total number of times the first advertisement was displayed. This quotient may be compared to the quotient of the second advertising campaign to allow comparisons of the effectiveness of one or more advertisements. In other embodiments, other types of return on investment calculations or measures of online advertising effectiveness may be used. By dividing the groups by the level of interactivity with the online advertising, the process may compare the treatment of the group viewed, to the treatment of the group clicked, to the treatment of the group redeemed, or to the treatment of the group not exposed, to determine the effectiveness of the online advertising.

Step measure effect 736 may calculate other metrics that may be used to analyze the effectiveness of online advertising, for example the rate of click-through rate and redemption for a specified medical diagnosis and treatment or how many of the people who were exposed to, or who actually clicked or redeemed, an advertisement actually suffer from a specified medical condition, comply with the prescription specified by their physician, or are insured (and, if so, the amount of any co-pay). For example, the system may allow comparing medication purchasing behavior among groups of people who were exposed to, or who clicked or redeemed, an online advertisement before and after the online advertising campaign. The comparison may include or exclude geographical regions based on the geographical targeting of other media advertising.

Figure 9D:
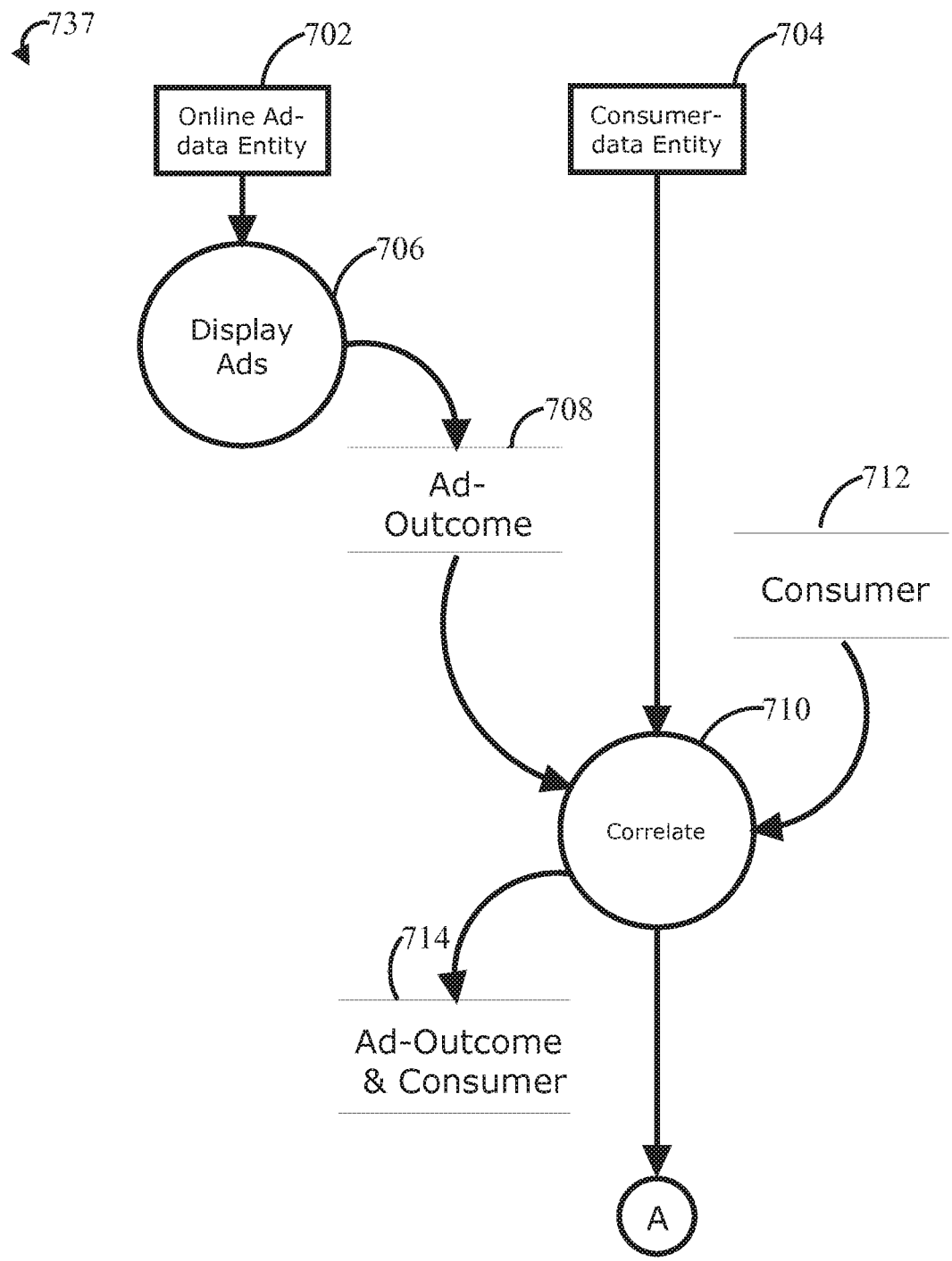
FIGS. 9D and 9E show a data flow diagram illustrating a series of steps to measure the effect of an online advertising campaign using Zip+4 codes, according to another embodiment.
Figure 9E:
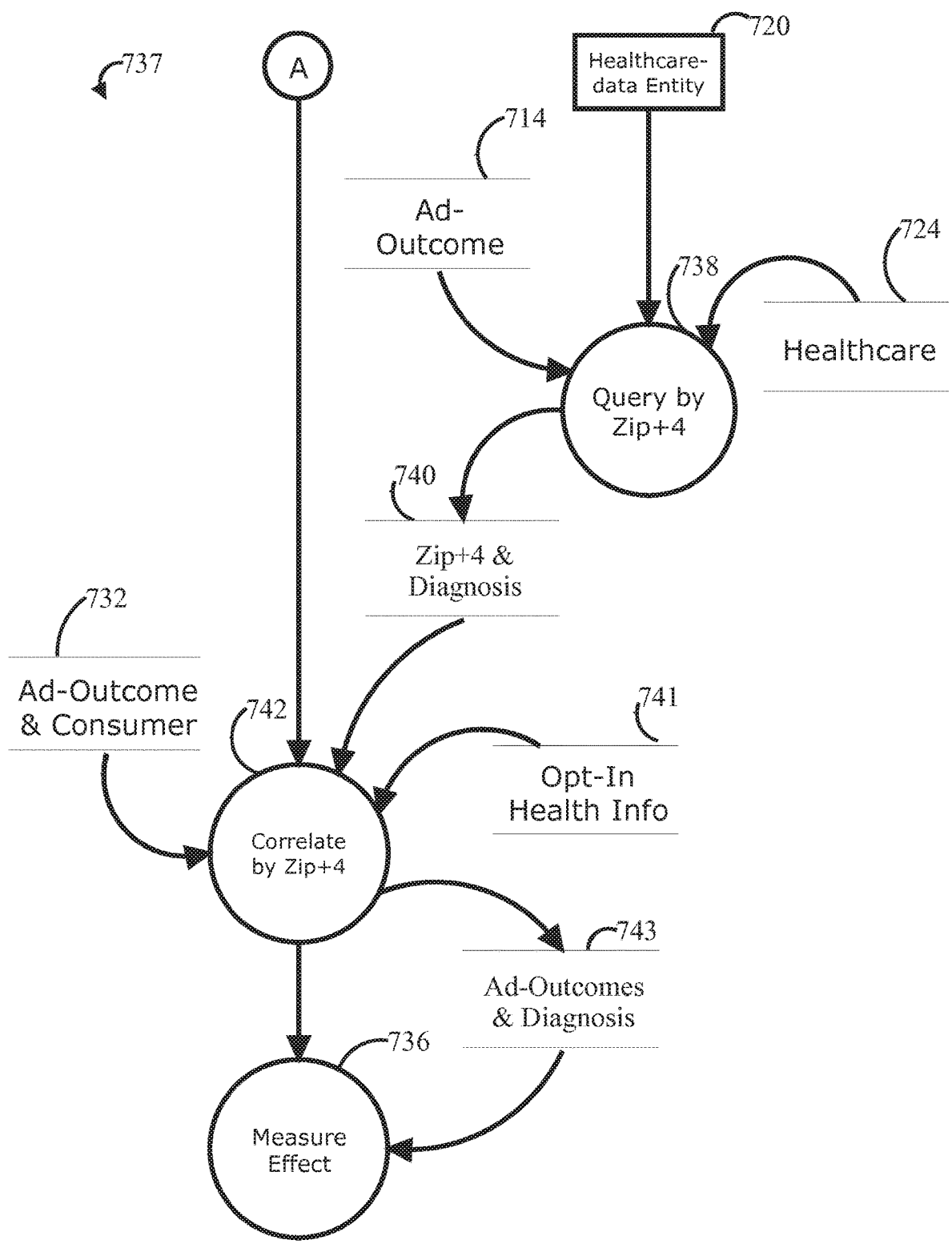

FIGS. 9D and 9E show a data flow diagram illustrating a series of steps of system 737 to measure the effect of an online advertising campaign using Zip+4 codes, according to another embodiment. System 737 may follow substantially similar steps and data flow as System 700 (see FIGS. 9A-9C), including the interaction between online-data entity 702 and consumer-data entity 704. FIGS. 9D and 9E are connected by the single, circled letter A.

FIG. 9E shows system 737 correlating or tabulating information from healthcare-data entity 720 using different steps and data. To correlate or tabulate healthcare database 724, healthcare-data entity 720 may perform step query by ZIP+4 738. Step query by ZIP+4 738 may query a test group and a control group from healthcare database 724 by using correlating information from ad-outcome and consumer database 714. This correlating information may include address information or identifying information such as a postal address or an online identifier. For example, the correlating information may be a ZIP+4 postal code. When using a ZIP+4 postal code, the information obtained from healthcare database 724 may not always precisely or accurately correspond to the individual who viewed the advertisement and whose data may be stored in ad-outcome and consumer database 714. Precise or high correspondence between healthcare database 724 and ad-outcome and consumer database 714 may not be required to measure the effectiveness of an online advertising campaign, because measuring the effectiveness of an online advertising campaign may occur, to a measurable degree of statistical certainty, without a direct correspondence between the individual whose data is represented in healthcare database 724 and ad-outcome and consumer database 714. In other words, it may be sufficient to know that a quantity of consumers within a geographic area have consumed the online advertising without knowing which individuals have consumed the treatment. In addition, this may help to maintain the privacy of the individuals who may be suffering from the health condition or receiving medical treatment, or who otherwise have protected healthcare information. Step query by ZIP+4 738 may write test group or control group information to ZIP+4 and treatments database 740. Zip+4 and treatments database 740 may include treatment results, which may be for a single treatment of a single patient, or which may tabulated among all patients within a geographical location such as a ZIP+4 postal code. Treatments database 740 may relate to treatment results to a Zip+4 postal code, a portion of a postal address, or an online identifier.

Step correlate by ZIP+4 742 may be performed by consumer-data entity 704. Step correlate by ZIP+4 742 may include information from the ZIP+4 and diagnosis database 740, ad-outcome and consumer database 732, and opt-in health info database 741. Opt-in health info database 741 may include information about a consumer's health from non-governmentally regulated sources such as online surveys that consumers may complete (through websites, email, or other electronic means) in response to advertisements, sweepstakes, or social networking. Opt-in health info database 741 may include information from membership organizations, such as the American Association of Retired People ("AARP"), which collect "opt-in" information from their membership. Opt-in health info database 741 may include information gathered from other non-governmentally regulated sources. Consumer-data entity 704 may use opt-in health info database 741 as an additional source for healthcare ailments and conditions, treatments, treatment results, and other healthcare information. Step correlate by ZIP+4 742 may also use both opt-in health info database 741 and ZIP+4 and treatments database 740 to assist measuring the effectiveness of the online advertising campaign by quantifying or summarizing the treatment results available in both databases. Step correlate by ZIP+4 742 may combine the treatment result information with the ad-outcome and consumer database 732 to provide data to ad-outcomes and diagnosis database 743.

System 737 may measure the effectiveness of the online advertising campaign during step measure effects 736. Step measure effect 736 may occur substantially as described above in connection with FIG. 9C. Step measure effect 736 may use data from ad-outcomes and diagnosis database 743. In various embodiments, different sources of healthcare information may be quantified or summarized. In some embodiments, treatment information (such as number of new patients, or the quantity of diagnosis) may be used. In other embodiments, diagnosis information (such as number of prescriptions or number of days of therapy) may be used. In still further embodiments, a combination of treatment and diagnosis information may be used.

Figure 10A:
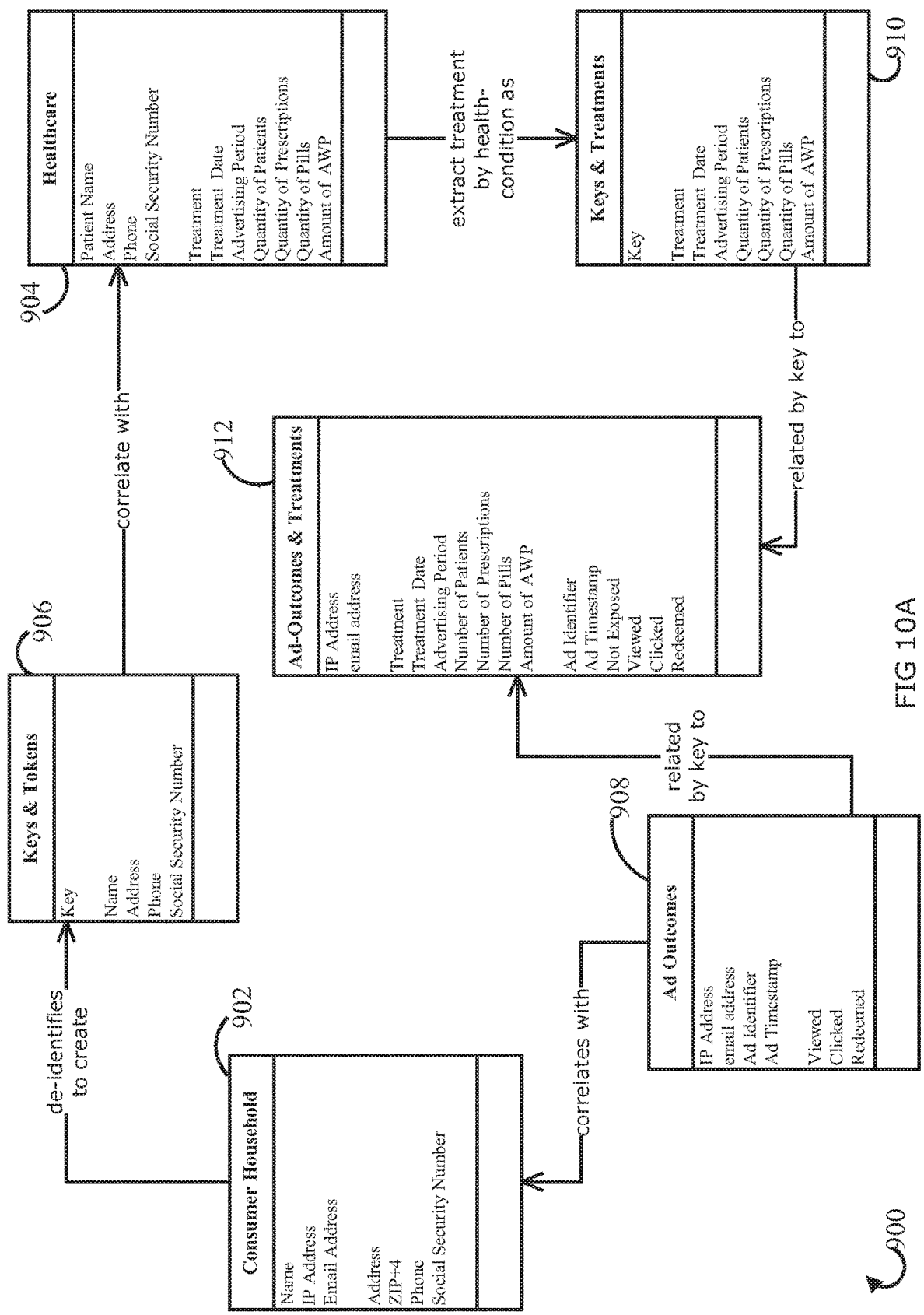
FIG. 10A shows a class diagram illustrating the relationships among healthcare database objects, consumer database objects, online advertising database objects, and other example objects, according to an embodiment.

FIG. 10A shows a class diagram illustrating the relationships among healthcare database objects, consumer database objects, online advertising database objects, and other example objects, according to an embodiment.

System 900 shows objects and their relationships to each other, as shown in FIG. 10A. Object consumer household 902 shows some example attributes that may be stored for consumer household information on behalf of a consumer-data entity. Object consumer household 902 may be similar to object consumer household 402 (see FIG. 4). Object consumer household 902 may include one or more online identifiers, such as Internet protocol address or e-mail address. Object consumer household 902 may include information related to a postal address, geographic location, phone number, Social Security number, or other information that may be helpful to identify the consumer. Object consumer household 902 may include information from consumer household databases. Object consumer household 902 may include information obtained from an "opt-in" or redemption process during the display of the online advertising. Object consumer household 902 may include information from commercial IP address databases that may be collected during other online activities or licensed/sold for use in targeting IP addresses.

Object healthcare 904 may be related to object consumer household 902 through object keys and tokens 906. Object healthcare 904 may correlate with keys and tokens 906 using similar attributes, information, relationships, and steps as described herein in connection with FIG. 4, including object consumer-household 402, object healthcare 404, and object keys-and-tokens 406. Object healthcare 904 may include treatment information, such as a new diagnosis, a new patient, number of pills used, number of prescriptions written, number of days of therapy, other prescription information, medical billing information, and other information that is related to the treatment or diagnosis of an illness or ailment. In some embodiments, object healthcare 904 may include detailed disease and treatment information on more than 100 million patients, which may be grouped into more than 35 million Zip+4 areas. Object consumer household 902 may include information that is not regulated as personal healthcare information. In some embodiments, object consumer household 902 may include detailed address information on as many households as possible; for example, using data from more than 150 million Internet-enabled device. The detailed address information may include IP addresses, email address, and postal or mailing addresses. In some embodiments, object consumer household 902 may include information supplied from the online advertising entity or online advertising webserver such as information captured during a redemption. In some embodiments, healthcare data may be sub-setted to include a statistically significant portion of healthcare data correlated to the set of keys, whereby a subset of healthcare data is formed. In some embodiments, healthcare data may include some falsified data that represents a statistically insignificant portion of the healthcare data.

In embodiments that calculate the effectiveness of online advertising, the object model may relate information associated with the outcome of an advertisement display to treatment information available in healthcare database. In FIG. 10A, object ad-outcomes 908 may be associated with object keys-and-treatments 910 through object ad-outcomes and treatments 912.

Object ad-outcomes 908 may be correlated with object consumer household 902 using information gathered during the display of the online advertisement, such as the IP address where the advertisement was displayed, the e-mail address where the advertisement was sent, or other online identifier used to deliver the advertisement to a potential consumer. Object ad-outcomes 908 may include other information collected at the time the advertisement was displayed, such as whether the consumer clicked a link in the advertisement, whether the consumer followed the advertisement to redeem, what time and date the ad was displayed, which advertisement was displayed to the potential consumer, what website the consumer was viewing when the advertisement was displayed, how long the advertisement was displayed, and any other metrics that may be gathered by an online advertising entity. Object ad-outcomes 908 may include an outcome-indicator to indicate the outcome of the online advertising, for example user clicked ad, user exposed to ad, user redeemed ad, or user viewed other websites with health information. This may allow the system to divide the set of healthcare data into at least four groups including a group that viewed, a group that clicked, a group that redeemed, and a group not exposed to online advertising. In other embodiments, other groupings may be used.

Object keys-and-treatments 910 may be extracted from object health care 904 using the ailment or health condition that the online advertisement endeavors to relieve or alleviate. Object keys-and-treatments 910 may include a key from the process of de-identifying the data in object health care 904. The key may be derived from the same process used to determine the key for the key of object keys-and-tokens 906. This may allow treatment information to be later related to information associated with the display of the online advertisement. Object keys-and-treatments 910 may include information related to treatment, such as whether or how many new diagnosis, new prescription information, refill prescription information, the date of treatment, number of display ad exposures, number of clicks, number of redemptions, number of prescriptions with a Zip+4 that received an ad exposure, monthly counts of new prescriptions and/or total prescriptions, grouping by time period (monthly, weekly, daily, before, or after), measure by brand percentage of market share. Object ad-outcomes and treatments 912 may include information needed to calculate the change in prescription volume and market share before and after the online advertising campaign within a group that is presently being treated for the health condition which is the subject of the online advertising. Object ad-outcomes and treatments 912 may include information needed to calculate the change in prescription volume and share within a group that is presently being treated for the health condition which is the subject of the online advertising. Object ad-outcomes and treatments 912 may allow for comparison to a control group of Zip+4's for the three groupings: exposed, clicked, and converted.

Figure 10B:
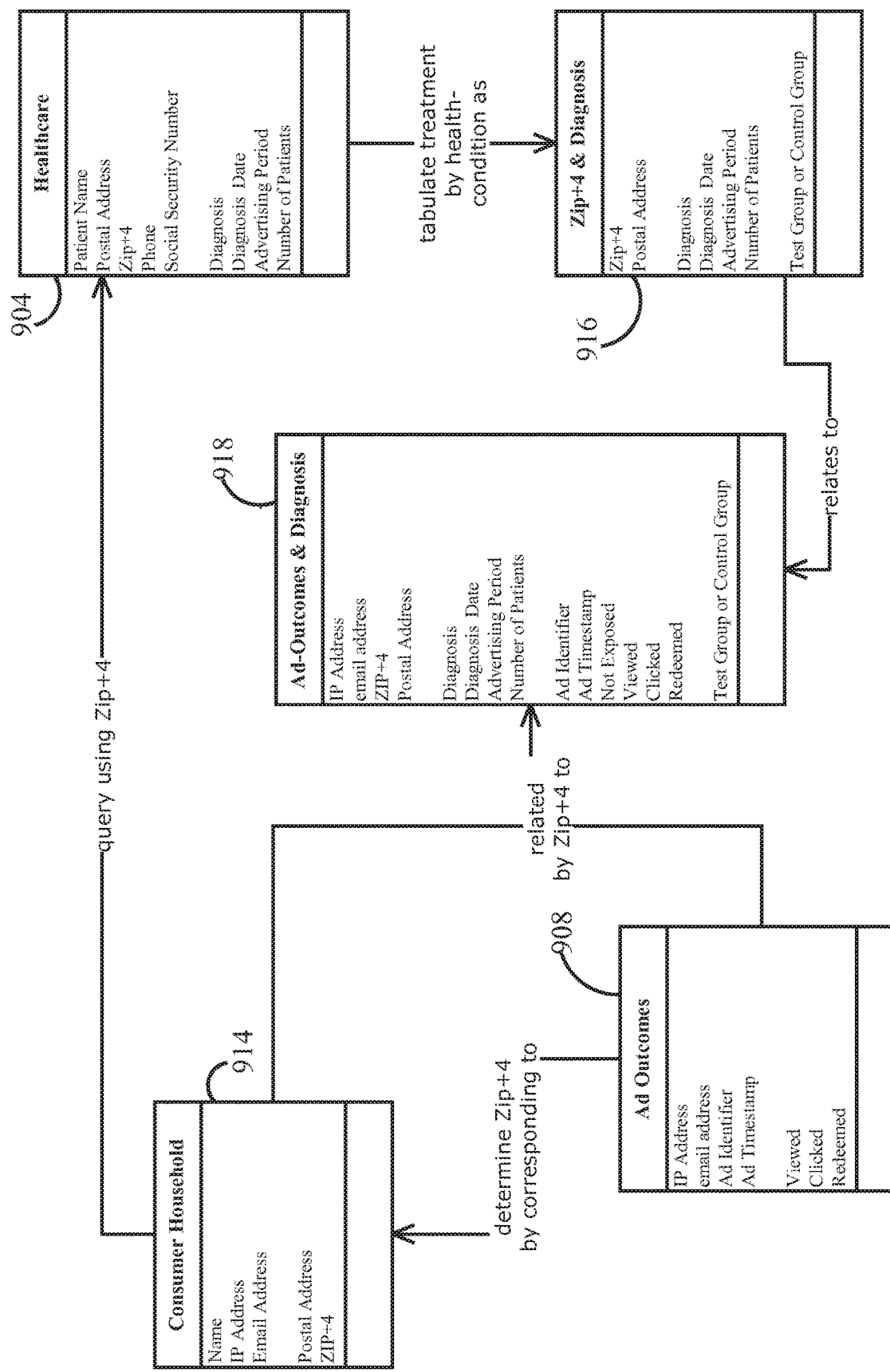
FIG. 10B shows a class diagram illustrating the relationships among healthcare database objects, consumer database objects, online advertising database objects, and other example objects, according to an embodiment.

FIG. 10B shows a class diagram illustrating the relationships among healthcare database objects, consumer database objects, online advertising database objects, and other example objects, according to an embodiment. System 913 shows objects and their relationships to each other. Object consumer household 914 shows example attributes that may be stored for consumer household information on behalf of the consumer data entity. Object consumer household 914 may include information related to online identifiers used by the consumer such as the consumer's IP addresses, the consumer's e-mail addresses, the consumer's web browser cookie information, and other information that may be used to identify the consumer online. In some embodiments, geographical indicator may be stored within, or embodied within an online identifier. For example, a ZIP+4 postal code may be placed within a web browser cookie. Object consumer household 914 may include information related to the geographic location of the consumer, such as the postal address, the ZIP+4 postal code, a portion of the postal address, latitude and longitude, and other information that may identify the geographical location of the consumer.

Object consumer household 914 may be related to object health care 904 by querying using geographically identifying information such as a ZIP+4 postal code. Object consumer household 914 may be related to object ad-outcomes 908 by correlating an online identifier from object ad-outcomes 908 to an online identifier in object consumer household 914.

Object ZIP+4 and treatments (not shown) may store a geographic identifier in connection with a treatment result for a consumer. Object ZIP+4 and treatments may store tabulated summary treatment results for consumers located at or within the geographic identifier. For example, object zip+4 and treatments may include a geographic identifier such as a ZIP+4 postal code, a postal address, or a portion of a postal address. Object ZIP+4 and treatment may include treatment results, including the treatment date or advertising period. Object ZIP+4 and diagnosis 916 may include tabulations, summarizations or amounts of patients, new diagnosis, prescriptions, or other quantification of diagnosis results. Objects ZIP+4 and diagnosis 916 may include information relating to diagnosis, results, and geographical identifier to a particular test group or control group or other grouping of treatment information that is useful to assist in the measurement of the effectiveness of the advertising campaign. Objects ZIP+4 and diagnosis 916 may be related to object healthcare 904 by querying or tabulating information in object health care 904.

Object ad-outcomes and diagnosis 918 shows example attributes that assist in the three-way correlation between the ad outcomes, the consumer household information, and the treatment results. Object ad-outcomes and diagnosis 918 may include attributes to identify the consumer, such as the online identifier, geographic identifier, or ZIP+4 postal code. Object ad-outcomes and diagnosis 918 may include attributes to quantify, summarize, or tabulate the treatment results. Object ad-outcomes and diagnosis 918 may include attributes to indicate the advertisement, ad campaign, or the ad outcome FIGS. 11A-11C show a data structure layout diagram illustrating example values of electronic lists for tracking information helpful in determining or measuring the outcome of a healthcare advertisement, according to an embodiment.

FIG. 11A shows a data structure layout for evaluating ad-outcomes in terms of diagnosis and treatments. Column Period indicates two or more different time periods, for example before and after exposure to the online advertising campaign. Column IP indicates the IP address of the device or computer connected to the Internet. Column IP may not have IP addresses or other online identifiers for the control group because the control group, by definition, likely did not see, did not respond, or was not tracked by the online advertising campaign. Column Ad indicates the online advertising campaign. Column Test or Control indicates the grouping of consumers, that is consumers who were exposed to the online advertising campaign as the test group or consumers who were not exposed the online advertising campaign. Columns New Patients, RXs, and AWP are summaries or tabulations of diagnosis or treatment results for the given period, IP address, ad campaign, and test or control group. Note that the example data and quantities are illustrative only and are intentionally simple to aid in understanding the calculation or measurement of the effectiveness of online advertising. Said another way, the diagnosis or treatment result values shown in the figure may not be indicative of actual treatment results.

FIG. 11B shows a data structure layout to calculate a return on investment value for the data contained in FIG. 11A. Column Impressions indicate the number of times an advertisement was displayed. Column Cost per Impression indicates the cost to display or the average cost to display an impression. Column Test/control Difference shows the difference between the average wholesale price ("AWP") of the treatments for the test group and the control group for each period. Column ROI shows the revenue increase attributable to online advertising as a percentage of the cost of the online advertising.

FIG. 11C shows a data structure layout to measure the effectiveness of one online advertising campaign relative to another online advertising campaign using the values of FIG. 11A. Column Ad indicates the online advertising campaign. Column Impressions indicates the number of advertisements that were displayed during the ad campaign. Column RXs indicates the treatment result as a quantity of prescriptions attributable to the online ad impressions for the related ad campaign. Column RXs/Impressions shows how many prescriptions are attributable to each impression.

Upon reading the teachings of this specification, those of ordinary skill in the art will realize that other methods of calculation may be selected that allow comparison between online advertising campaigns, offline advertising campaigns, mixes of media, advertising messages, targeting profiles, and other advertising techniques, by using diagnosis or treatment results and considering such factors as online media type, consumer preferences, economic considerations, advances in advertising tracking technology, advances in advertising display technology, and other factors.

Figure 12:
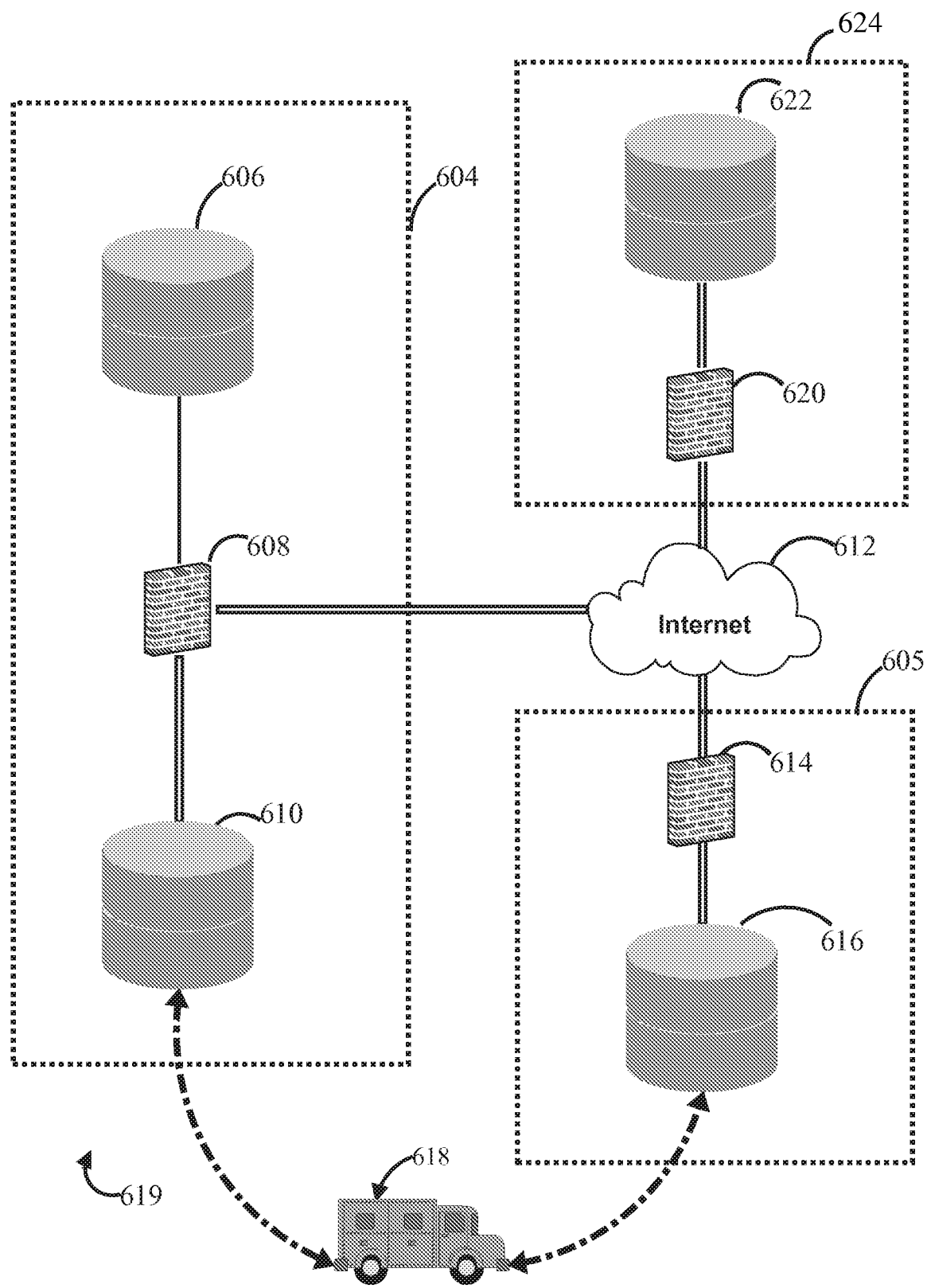
FIG. 12 shows a network architecture diagram illustrating a computer system configured to determine the effectiveness of online advertising, according to an embodiment.

FIG. 12 shows a network architecture diagram illustrating computer system 619 configured to determine the effectiveness of online advertising, according to an embodiment. Computer system 619 may be similar to system 600. Computer systems 619 may include online advertising entity 618. Online advertising entity 624 may store ad-outcome data on ad outcome database 622. Online advertising entity 624 and may include security measures 620. Although this diagram shows operation of databases by three separate entities, in other embodiments, databases may be operated by a single entity or by more than three entities, which may depend on factors such as economic considerations, efficiency considerations, governmental regulations of the data or data holder, or requirements of third parties.

Although this specification describes the inventor's best mode and other embodiments, it will be understood that the broadest scope of the disclosed embodiments includes such modifications as diverse application of technology, variance of method steps, choice of software architecture, selection of targeting message methods, varying business methods, varying statistical methods, and other method steps. Such scope is limited only by the below claims as read in connection with the above specification. Further, many other advantages will be apparent to those skilled in the art from the detailed descriptions and the claims.

What is claimed is:

1. A computerized method having practical use in improved targeting of advertisement messages for display on consumer devices, which improved targeting utilizes non-personalized geographic healthcare condition data, the method comprising:

with a programmed computer system including at least one processor and at least one memory:

(a) for each of a plurality of geographic identifiers, each geographic identifier denoting a respective one of a plurality of geographic areas, producing targeting data by:

(i) using a combination dataset containing personal health data from a first database and personal consumer data from a second database, wherein:

(A) the personal health data from the first database and the personal consumer data from the second database have been combined by use of a set of individual keys, each key identifying one of a multitude of persons;

(B) the personal health data from the first database associates the individual keys with one of a set of healthcare condition codes, wherein each of the healthcare condition codes uniquely represents one of a plurality of healthcare conditions of interest, thereby indicating which of the persons identified by the individual keys has which of the healthcare conditions of interest, and (C) the personal consumer data from the second database associates the individual keys with the geographic identifiers, thereby which of the persons identified by the individual keys resides in which of the geographic areas; and (ii) linking the geographic identifier with a set of aggregate numerical values, determined using the combination dataset, wherein respective of the aggregate numerical values are based on the number of persons, in the geographic area denoted by the geographic identifier, who are associated with respective of the healthcare condition codes, whereby each of the set of aggregate numerical values represents prevalence in the geographic area of respective healthcare conditions of interest associated with the respective healthcare condition codes;

(iii) wherein the targeting data does not contain personally identifiable information (PII) from the first database or the second database; and (b) removing from the targeting data information pertaining to those geographic areas and specific healthcare condition codes that would permit re-identification of persons in the geographic area associated with respective of the healthcare condition codes; and (c) after part (b), using the targeting data to cause direction of an advertisement message for display on a plurality of consumer devices associated with each of a plurality of the geographic areas, based on prevalence in each of the plurality of geographic areas of one of the plurality of healthcare conditions of interest, which prevalence is based on the targeting data.

2. The method of claim 1 wherein the removed targeting data that would permit re-identification in part (a)(iii) comprises data related to any geographic area containing only one person.

3. The method of claim 1 wherein the removed targeting data that would permit re-identification in part (a)(iii) comprises data related to any geographic area in which all of the individual keys associated with the identifier for the geographic area are associated with at least one of the healthcare condition codes, thereby indicating that all of the persons identified by the individual keys in the geographic area have the healthcare condition.

4. The method of claim 1 wherein the consumer data from the second database associates the individual keys with the geographic identifiers based on IP addresses of consumer devices connected to the individual keys.

5. The method of claim 1 further comprising receiving, from a third-party entity, a certification that the process implemented by the computer system is in compliance with privacy regulations.

6. The method of claim 1 wherein the geographic areas are areas identified by nine-digit Zip+4 (Zone Improvement Program plus four digits) codes.

7. The method of claim 1 wherein the geographic areas are city blocks.

8. The method of claim 1 wherein the geographic areas are multi-unit buildings.

9. The method of claim 1 wherein the personal health data from the first database is known to contain some falsified data records, but the programmed computer system does not have access to data indicating which records of the first database are the falsified data records.

10. The method of claim 1 wherein the aggregate numerical values are percentages.

11. A computer system connected and programmed for improved targeting of advertisement messages for display on consumer devices, which improved targeting utilizes non-personalized geographic healthcare condition data, the computer system programmed to:

(a) for each of a plurality of geographic identifiers, each geographic identifier denoting a respective one of a plurality of geographic areas, produce targeting data by:

(i) using a combination dataset containing personal health data from a first database and personal consumer data from a second database, wherein:

(A) the personal health data from the first database and the personal consumer data from the second database have been combined by use of a set of individual keys, each key identifying one of a multitude of persons;

(B) the personal health data from the first database associates the individual keys with one of a set of healthcare condition codes, wherein each of the healthcare condition codes uniquely represents one of a plurality of healthcare conditions of interest, thereby indicating which of the persons identified by the individual keys has which of the healthcare conditions of interest, and (C) the personal consumer data from the second database associates the individual keys with the geographic identifiers, thereby indicating which of the persons identified by the individual keys resides in which of the geographic areas; and (ii) linking the geographic identifier with a set of aggregate numerical values, determined using the combination dataset, wherein respective of the aggregate numerical values are based on the number of persons, in the geographic area denoted by the geographic identifier, who are associated with respective of the healthcare condition codes, whereby each of the set of aggregate numerical values represents prevalence in the geographic area of respective healthcare conditions of interest associated with the respective healthcare condition codes;

(iii) wherein the targeting data does not contain personally identifiable information (PII) from the first database or the second database; and (b) remove from the targeting data information pertaining to those geographic areas and specific healthcare condition codes that would permit re-identification of persons in the geographic area associated with respective of the healthcare condition codes; and (c) after part (b), use the targeting data to cause direction of an advertisement message for display on a plurality of consumer devices associated with each of a plurality of the geographic areas, based on prevalence in each of the plurality of geographic areas of one of the plurality of healthcare conditions of interest, which prevalence is based on the targeting data.

12. The computer system of claim 11 wherein the removed targeting data that would permit re-identification in part (a)(iii) comprises data related to any geographic area containing only one person.

13. The computer system of claim 11 wherein the removed targeting data that would permit re-identification in part (a)(iii) comprises data related to any geographic area in which all of the individual keys associated with the geographic identifier for the geographic area are associated with at least one of the healthcare condition codes, thereby indicating that all of the persons identified by the individual keys in the geographic area have the healthcare condition.

14. The computer system of claim 11 wherein the consumer data from the second database associates the individual keys with the geographic identifiers based on IP addresses of consumer devices connected to the individual keys.

15. The computer system of claim 11 wherein the geographic areas are areas identified by nine-digit Zip+4 (Zone Improvement Program plus four digits) codes.

16. The computer system of claim 11 wherein the personal health data from the first database is known to contain some falsified data records, but the programmed computer system does not have access to data indicating which records of the first database are the falsified data records.

\* \* \* \* \*

UNITED STATES PATENT AND TRADEMARK OFFICE
CERTIFICATE OF CORRECTION

| | | |
|---|---|---|
| PATENT NO. | : 11,521,746 B1 | |
| APPLICATION NO. | : 16/382989 | |
| DATED | : December 6, 2022 | |
| INVENTOR(S) | : Michael D. Weintraub | |

It is certified that error appears in the above-identified patent and that said Letters Patent is hereby corrected as shown below:

In the Claims

In Column 21, Line 47 (Claim 1), after "thereby" insert --indicating--
In Column 23, Line 23 (Claim 11), change "remove" to --removing--
In Column 23, Line 28 (Claim 11), change "use" to --using--

Signed and Sealed this
Seventeenth Day of January, 2023

*Katherine Kelly Vidal*

Katherine Kelly Vidal
*Director of the United States Patent and Trademark Office*